United States Patent
Sato

(12) 
(10) Patent No.: US 6,334,232 B1
(45) Date of Patent: Jan. 1, 2002

(54) TOOTHBRUSH AND ELECTRIC TOOTHBRUSH

(76) Inventor: Masanori Sato, 105-5, Oaza-kawado, Sakurae-cho, Ohchi-gun, Shimane (JP)

(*) Notice: Subject to any disclaimer, the term of this patent is extended or adjusted under 35 U.S.C. 154(b) by 0 days.

(21) Appl. No.: 09/609,252

(22) Filed: Jun. 30, 2000

Related U.S. Application Data

(62) Division of application No. 09/084,098, filed on May 26, 1998, now Pat. No. 6,209,164, which is a division of application No. 08/963,114, filed on Oct. 28, 1997, now Pat. No. 5,842,249, which is a continuation of application No. 08/424,314, filed as application No. PCT/JP93/01561 on Oct. 28, 1993, now abandoned.

(30) Foreign Application Priority Data

| Oct. 31, 1992 | (JP) | ............................................. 4-316113 |
| Nov. 30, 1992 | (JP) | ............................................. 4-345559 |
| Dec. 29, 1992 | (JP) | ............................................. 4-360533 |
| Oct. 4, 1993 | (JP) | ............................................. 5-273202 |

(51) Int. Cl.[7] ................................................. A46B 9/04
(52) U.S. Cl. ..................... 15/167.2; 15/167.1; 15/172; 15/22.1; 15/201
(58) Field of Search .......................... 15/167.2, 167.1, 15/DIG. 5, 207.2, 201, 172, 22.1; D4/105, 106

(56) References Cited

U.S. PATENT DOCUMENTS

| 887,181 | A | | 5/1908 | Barnes ........................ 15/167.2 |
| 1,270,233 | A | | 6/1918 | Stoorman .................... 15/167.2 |
| 1,707,118 | A | | 3/1929 | Goldberg .................... 15/167.2 |
| 1,709,262 | A | | 4/1929 | Henderhan ................. 15/167.2 |
| 1,830,995 | A | * | 11/1931 | Genn ......................... 15/167.2 |
| 1,868,368 | A | | 7/1932 | Reese ......................... 15/167.2 |
| 2,066,241 | A | | 12/1936 | Trattner et al. ............ 15/167.2 |
| 2,093,383 | A | | 9/1937 | Rudof et al. ................ 15/167.2 |
| 2,214,407 | A | * | 9/1940 | Deutsch ...................... 15/167.2 |
| 2,588,601 | A | * | 3/1952 | Zavagno ..................... 15/167.2 |
| 2,682,066 | A | | 6/1954 | Keely .......................... 15/167.2 |
| 2,701,380 | A | * | 2/1955 | Ripper ........................ 15/167.2 |

(List continued on next page.)

FOREIGN PATENT DOCUMENTS

| DE | 825536 | | 12/1951 | |
| EP | 0101618 | A2 | 2/1983 | |
| FR | 588348 | | 5/1925 | |
| FR | 1126824 | | 12/1956 | |
| FR | 2489119 | | 3/1982 | |
| GB | 9632 | * | 5/1902 | ................ 15/167.2 |
| GB | 402293 | | 11/1933 | |
| GB | 483939 | * | 4/1938 | ................ 15/167.2 |
| IT | 323786 | * | 3/1936 | ................ 15/167.2 |
| IT | 584669 | | 11/1958 | |
| JP | 54-83976 | | 6/1979 | |
| JP | 55-108310 | | 8/1980 | |
| JP | 59-739913 | | 5/1984 | |
| JP | 61-86038 | | 6/1986 | |
| JP | 61-156526 | | 9/1986 | |
| JP | 61-55963 | | 11/1986 | |
| JP | 62-136826 | | 8/1987 | |
| WO | 89/01303 | | 2/1989 | |
| WO | 8906528 | * | 7/1989 | ................ 15/167.2 |
| WO | 13691 | | 7/1993 | |

OTHER PUBLICATIONS

Oral Logic, Inc., Dentrust Brochure entitled "The Next Generation in Toothbrush Technology", 6 pgs.

Primary Examiner—Gary K. Graham
(74) Attorney, Agent, or Firm—Armstrong, Westerman, Hattori, McLeland & Naughton, LLP

(57) ABSTRACT

A toothbrush for removing plaque, tarter and calculus from teeth. The toothbrush includes an elongated grip handle having a plurality of toothbrush bodies mounted on an end. The toothbrush bodies are adapted to clean various surfaces of teeth simultaneously.

6 Claims, 19 Drawing Sheets

U.S. PATENT DOCUMENTS

| | | | |
|---|---|---|---|
| 2,771,624 A | 11/1956 | Ripper | 15/167.2 |
| 3,065,479 A | 11/1962 | McGee | 15/167.2 |
| 3,683,442 A * | 8/1972 | Holly | 15/167.1 |
| 4,131,967 A | 1/1979 | Northemann et al. | 15/167.2 |
| 4,223,417 A | 9/1980 | Solow | 15/167.2 |
| 4,375,115 A | 3/1983 | Zimmerman | 15/167.2 |
| 4,757,570 A | 7/1988 | Haeusser et al. | 15/167.2 |
| D315,450 S * | 3/1991 | Wagner | D4/106 |
| 5,072,481 A * | 12/1991 | Weyer | 15/167.2 |
| 5,137,039 A | 8/1992 | Klinkhammer | 15/167.2 |
| 5,305,491 A | 4/1994 | Hegemann | 15/167.2 |

\* cited by examiner

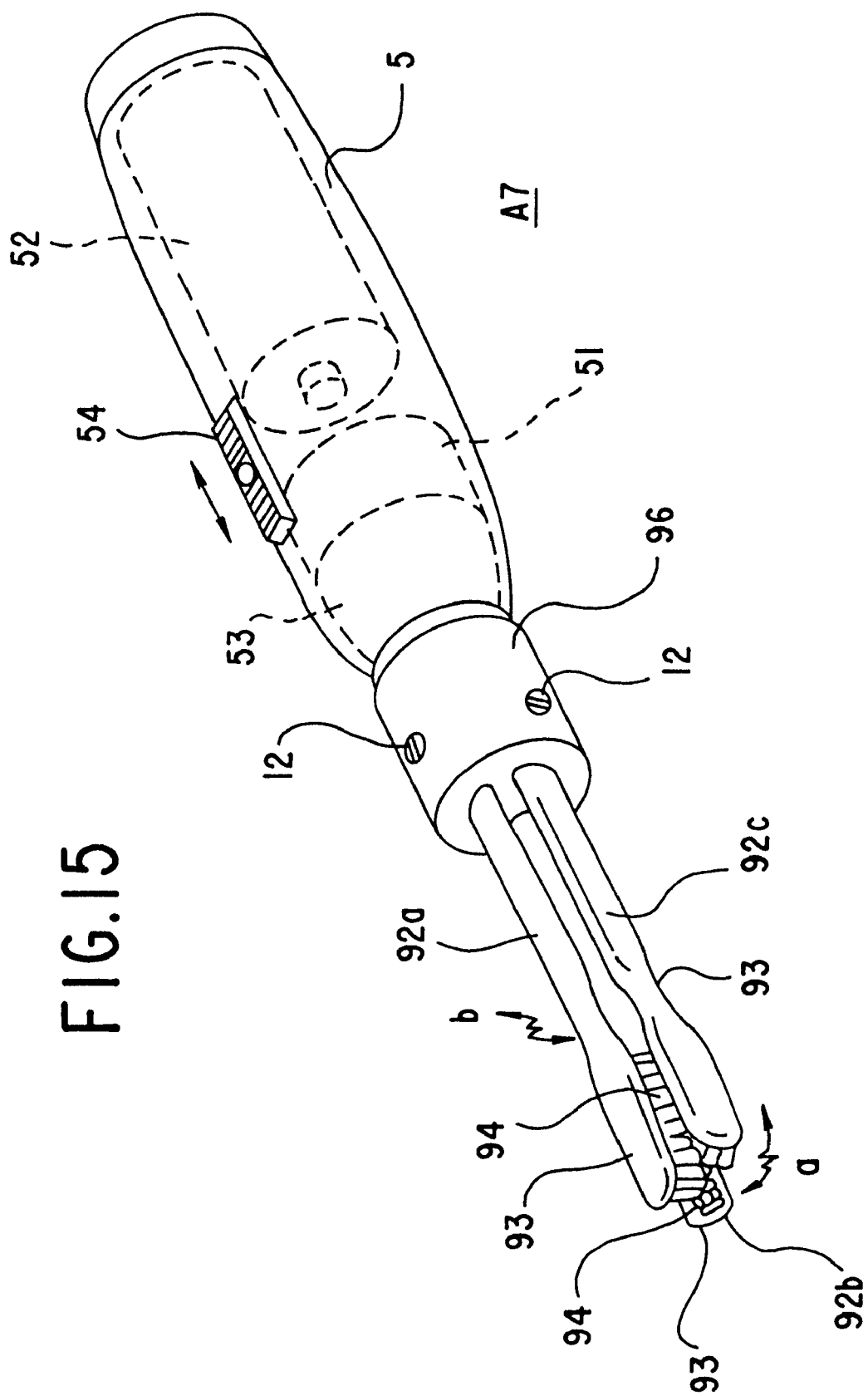

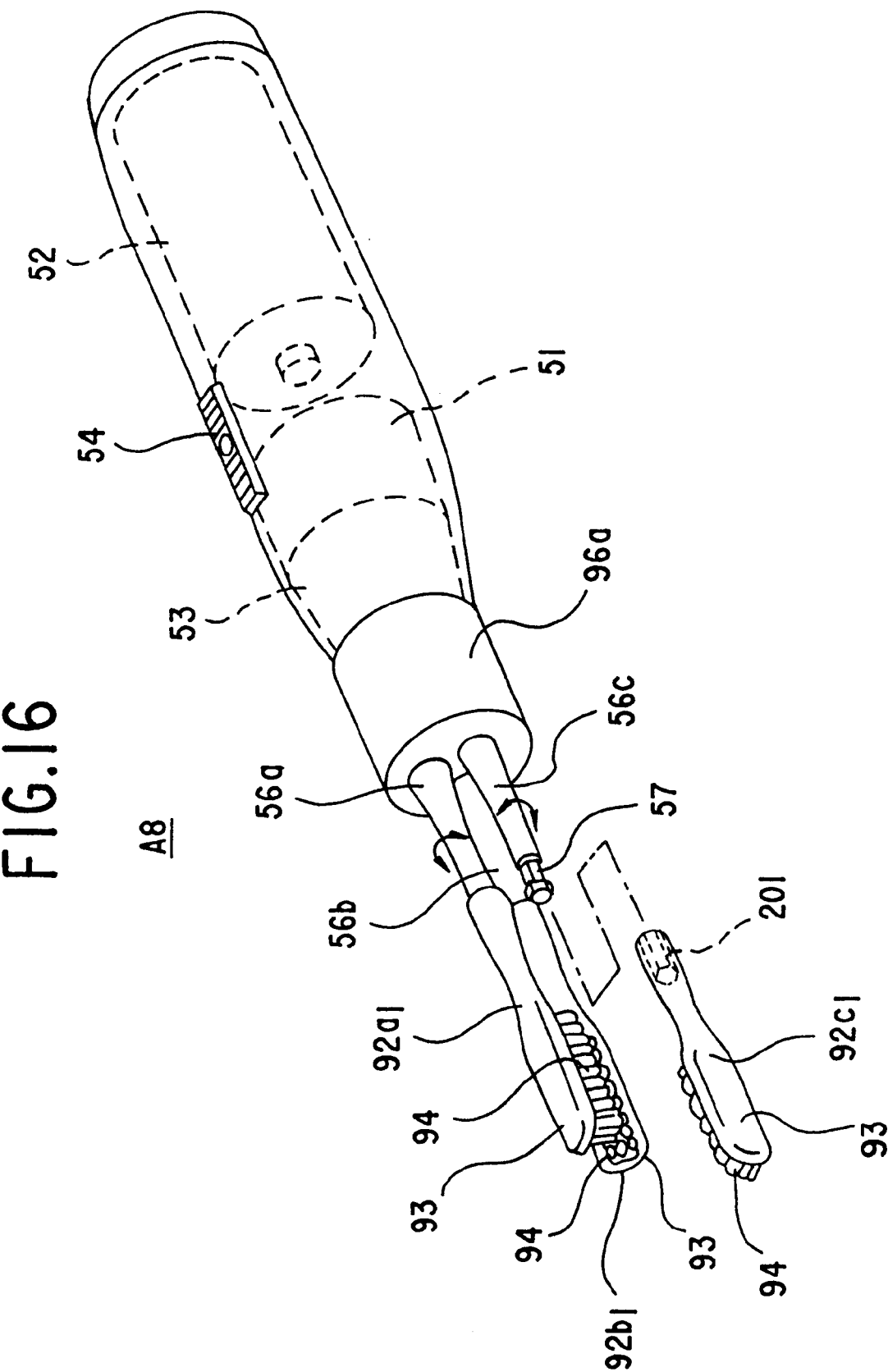

TOOTHBRUSH AND ELECTRIC TOOTHBRUSH

This application is a division of prior application Ser. No. 09/084,098 filed May 26, 1998, now U.S. Pat. No. 6,209, 164, which is a division of application Ser. No. 08/963,114 filed Oct. 28, 1997, now U.S. Pat. No. 5,842,249, which is a file wrapper continuation application of Ser. No. 08/424, 314 filed on Apr. 21, 1995, now abandoned, which is a national stage application under §371 of international application PCT/JP93/01561 filed Oct. 28, 1993.

FIELD OF THE INVENTION

The present invention relates to a toothbrush and an electric toothbrush for efficiently removing plaque, tartar, and calculus from teeth.

BACKGROUND OF THE INVENTION

Teeth are an important organ indispensable for the mastication of food and the utterance of speech sounds. In order for the teeth to perform their functions, it is necessary for them to be brushed after meals or before sleeping to prevent tartar and calculus from being deposited on dental necks for protection against periodontites.

For brushing teeth, it has heretofore been customary to use tooth brushes having bristle assemblies planted on an end of a handle. Electric toothbrushes that have been developed in recent years have also been widely used.

Toothbrushes and electric toothbrushes, which are respectively manually and automatically operable, are generally used by turning the bristle assemblies back and forth about the toothbrush axis.

However, the conventional toothbrushes and electric toothbrushes have suffered the following drawbacks:

When the handle of a toothbrush is rocked about its own axis in use, the bristle assemblies are angularly moved alternately upwardly and downwardly. More specifically, when the user of an electric toothbrush holds its grip cylinder and angularly moves the bristle assemblies about the axis while keeping the bristle assemblies against a tooth side or neck, a downward swinging movement of the bristle assemblies peels an end of the gum off the tooth neck, and pushes a deposit of plaque into a recess that is formed between the peeled gum and the tooth neck. Therefore, the brushing operation tends to produce a deposit of tartar and calculus, causing periodontites such as a dentoalveolitis.

SUMMARY OF THE INVENTION

Means according to the present invention for solving the above problems are as follows:

According to a first invention, a toothbrush comprises:
  a grip handle;
  a crown cap mounted on a distal end of the grip handle and having a substantially L-shaped cross section and a predetermined length; and
  bristle assemblies planted on inner surfaces of wings of the crown cap and having tip ends inclined at a predetermined angle toward a bent corner of the crown cap.

According to a second invention, an electric toothbrush comprises:
  a grip base;
  a handle mounted on the grip base for reciprocating angular movement at least about an axis thereof by electric actuator means housed in the grip base;
  a crown cap mounted on a distal end of the handle and having a substantially L-shaped cross section. and a predetermined length; and
  bristle assemblies planted on inner surfaces of wings of the crown cap and having tip ends inclined at a predetermined angle toward a bent corner of the crown cap.

According to a third invention, in the toothbrush or the electric toothbrush according to the first or second invention, the crown cap has adjusting means for adjusting the projection of one of the bristle assemblies, and mounting means for mounting a distal end of the grip handle or the handle detachably on a longitudinal end of the crown cap.

The electric actuator means is not limited to any structure, but may comprise a known means such as a combination of a motor and a cam mechanism.

The mounting means for detachably mounting the grind handle or the handle on the crown cap is not limited any particular structure. The mounting means may be composed of known means, e.g., engaging holes defined in the opposite ends of the crown cap and an engaging body mounted on the distal end of the grip handle or the handle and engaging in one of the engaging holes, or alternatively, an engaging hole defined longitudinally through the crown cap and an engaging shaft mounted on the distal end of the grip handle or the handle and engaging in the engaging hole.

The bristle assemblies are inclined at an angle of 45°, for example, to the inner surfaces of the crown cap. However, the angle of inclination is not limited to 45°. The bristle assemblies are not limited to any particular length, but may have the same length or lengths that vary stepwise.

The adjusting means for adjusting the projection of one of the bristle assemblies is not limited to any particular structure, but may be known means, e.g., a screw for moving a base on which the bristle assembly is planted into and out of the crown cap.

According to a fourth invention, a toothbrush comprises:
  a grip handle;
  a crown cap mounted on a distal end of the grip handle and including a molar tooth fitting portion and a front tooth fitting portion which have respective inner walls corresponding to respective tooth surfaces; and
  bristle assemblies planted on the inner walls of the molar tooth fitting portion and the front tooth fitting portion and inclined at an angle ranging from 30° to 60° toward tip ends of molar and front teeth that are fitted in the molar tooth fitting portion and the front tooth fitting portion, respectively.

According to a fifth invention, an electric toothbrush comprises:
  a grip base;
  a handle mounted on the grip base for reciprocating angular movement about an axis thereof or in the direction of a tooth axis, or in the direction normal to the direction of the tooth axis, by electric actuator means housed in the grip base;
  a crown cap mounted on a distal end of the handle and including a molar tooth fitting portion and a front tooth fitting portion which have respective inner walls corresponding to respective tooth surfaces; and
  bristle assemblies planted on the inner walls of the molar tooth fitting portion and the front tooth fitting portion and inclined at an angle ranging from 30° to 60° toward tip ends of molar and front teeth that are fitted in the molar tooth fitting portion and the front tooth fitting portion, respectively.

According to a sixth invention, in the toothbrush or the electric toothbrush according the fourth or fifth invention, the crown cap has only a molar tooth fitting portion and a bristle assembly corresponding thereto.

According to a seventh invention, in the toothbrush or the electric toothbrush according the fourth or fifth invention, the crown cap has only a front tooth fitting portion and a bristle assembly corresponding thereto.

The electric actuator means is not limited to any structure, but may comprise a known means such as a combination of a motor and a cam mechanism.

The bristle assemblies should preferably be inclined at an angle of 45° to the surfaces of a molar or front teeth that is fitted in the tooth fitting portion. However, the angle of inclination is not limited to 45°, but may be selected in a range from 30° to 60°. The bristle assemblies are not limited to any particular length, but may have the same length or lengths that vary stepwise.

According to an eighth invention, a toothbrush comprises:
  a grip handle; and
  a plurality of toothbrush bodies detachably mounted on a distal end of the grip handle;
  the toothbrush bodies having bristle assemblies inclined at an angle ranging from 30° to 60° with respect to sides of teeth toward tip ends of the teeth in use.

According to a ninth invention, a toothbrush comprises:
  a grip base;
  a vibrator mounted on the grip base for vibration in predetermined directions by electric actuator means housed in the grip base; and
  a plurality of toothbrush bodies detachably mounted on the vibrator;
  the toothbrush bodies having bristle assemblies inclined at an angle ranging from 30° to 60° with respect to sides of teeth toward tip ends of the teeth in use.

The electric actuator means is not limited to any structure, but may comprise a known means such as a combination of a motor and a cam mechanism.

The toothbrush bodies should preferably be attached such that the bristle assemblies are inclined at an angle of 45° with respect to sides of teeth that are inserted. However, the angle of inclination is not limited to 45°, but may be selected in a range from 30° to 60°.

The number of toothbrush bodies may generally range from two to three though not limited to any particular value. If two toothbrush bodies are employed, then they are positioned respectively on the corresponding opposite sides of teeth, or one of them is positioned on the occlusal tooth area of the teeth and the other on one of the sides of the teeth. If three toothbrush bodies are employed, then one of them is positioned on the occlusal tooth area of the teeth and the others on the respective sides of the teeth.

If the angle of inclination of the bristle assemblies were less than 30° or greater than 60°, then they would not sufficiently scrape off plaque or the like because the pressure applied by the tip ends of the bristle assemblies to the tooth surfaces would be weak.

The bristle assemblies are not limited to any particular length, but may have the same length or lengths that vary stepwise.

According to tenth through sixteenth inventions, an electric toothbrush 10 comprises a bristle assembly 16 reciprocally angularly movable to swing upwardly along teeth sides while being held against the teeth sides or neighboring regions, reciprocally rocking means 18 for angularly moving the bristle assembly 16, and an actuator 68 coupled to the reciprocally rocking means 18 (The reference numerals used in this sentence are indicated in FIG. 23, and those in sentences given below are indicated in FIG. 4).

The bristle assembly 16 may be mounted in one side of a casing 14 having a substantially inverted L shape, and a temporary positioning member 54 may be mounted on the other side of the casing 14 for temporarily positioning the bristle assembly 16 for engagement with a tooth side.

The temporary positioning member 54 may comprise a resilient member.

The temporary positioning member 54 may comprise bristles.

The temporary positioning member 54 may be adjustable in height.

The bristle assembly 16 may comprise an upper set of bristles 46 and a lower set of bristles 46, the lower set of bristles 46 being longer than the upper set of bristles 46.

The bristle assembly 16 comprises an upper set of bristles 46, a middle set of bristles 46, and a lower set of bristles 46, the bristles being of longer, shorter, and medium lengths successively from the lower set through the middle set to the upper set.

In the first through third inventions, when the toothbrush is used, one of the bristle assemblies is held against the occlusal tooth areas of teeth and the other against the boundaries (tooth necks) between the tooth sides and the gum. If the toothbrush is a manual toothbrush, then the grip handle is manually angularly moved reciprocally about the axis thereof. If the toothbrush is an electric toothbrush, the grip handle is angularly moved reciprocally about the axis thereof by the electric actuator means.

If the toothbrush has the adjusting means for adjusting the projection of one of the bristle assemblies, then the projection of the bristle assembly is adjusted by the adjusting means such that the bristle assembly adjustable by the adjusting means will abut against the occlusal tooth areas of teeth and the other bristle assemblies will abut reliably against the boundaries (the tooth necks) between the tooth sides and the gum.

The toothbrush with the adjusting means has a particular orientation in order to keep the adjustable bristle assembly in abutment against the occlusal. tooth areas of teeth at all times. In this structure, therefore, the crown cap can be attached in a different position. to change the orientation of the toothbrush for brushing all the surfaces of teeth. Specific details will be described later with respect to embodiments given below.

In the fourth through seventh inventions, when the toothbrush is used, a molar tooth is fitted in the molar tooth fitting portion or a front tooth is fitted in the front tooth fitting portion. Each of the bristle assemblies is held in contact with the surface of the tooth at an angle ranging from 30° to 60°. If the toothbrush is a manual toothbrush, then the grip handle is manually angularly moved reciprocally about the axis thereof, or in the direction of the tooth axis, or in the direction normal thereto. If the toothbrush is an electric toothbrush, the grip handle is angularly moved reciprocally about the axis thereof, or in the direction of the tooth axis, or in the direction normal thereto, by the electric actuator means.

In the eighth and ninth inventions, when the toothbrush is used, a tooth is fitted in the space surrounded by the bristle assemblies. The bristle assemblies positioned on tooth sides are held in contact with the tooth sides at an angle ranging from 30° to 60°. If the toothbrush is a manual toothbrush, then the grip handle is manually vibrated about the axis thereof, or in the direction of the tooth axis, or in the direction normal thereto. If the toothbrush is an electric toothbrush, the grip handle is vibrated about the axis thereof, or in the direction of the tooth axis, or in the direction normal thereto, by the electric actuator means.

In the tenth through sixteenth inventions, when the electric toothbrush is used to brush a tooth, the bristle assembly is brought into abutment against a side or neck of the tooth while being held substantially horizontally, and angularly moved reciprocally so as to swing upwardly by the reciprocally rocking means coupled to the actuator.

The bristle assembly may be mounted in one side of the casing of a substantially inverted L shape, and the temporary positioning member may be mounted on the other side of the casing for temporarily positioning the bristle assembly for engagement with the tooth side. The temporary positioning member can be held against the occlusal tooth area of the tooth crown for thereby accurately holding the bristle assembly against the tooth side or the tooth neck for scraping off deposited plaque.

The temporary positioning member may comprise a resilient member or bristles, and may be adjustable in height. This arrangement allows the temporary positioning member to hold the bristle assembly accurately against a tooth surface ranging from the tooth side to the tooth neck without slipping over the occlusal tooth area of the tooth crown.

The bristle assembly may comprise an upper set of bristles and a lower set of bristles, the lower set of bristles being longer than the upper set of bristles. Alternatively, the bristle assembly may comprise an upper set of bristles, a middle set of bristles, and a lower set of bristles, the bristles being of longer, shorter, and medium lengths successively from the lower set through the middle set to the upper set. With this arrangement, the bristles of the bristle assembly can abut against a curved tooth surface along the tooth side and the tooth neck for effectively removing plaque.

In any of the first through sixteenth inventions, since the bristle assemblies, though they are angularly movable reciprocally, are planted so as to be inclined to the tooth surface, the frictional force is stronger upon angular movement toward the tip end of the tooth, and weaker upon angular movement in the opposite direction. Therefore, plaque, tartar, and calculus deposited on the occlusal tooth area, the tooth side, and the tooth neck are gathered toward the center of the tooth fitting portion. For the same reason, the gum is not peeled off the tooth neck, and plaque, tartar, and calculus deposited, on the tooth neck are removed without being pushed between the tooth and the gum.

DESCRIPTION OF THE DRAWINGS

FIG. 15 is a perspective view of an electric toothbrush according to the present invention;

FIG. 16 is an exploded perspective view of an electric toothbrush according to another embodiment of the present invention;

DETAILED DESCRIPTION

Figure 1:
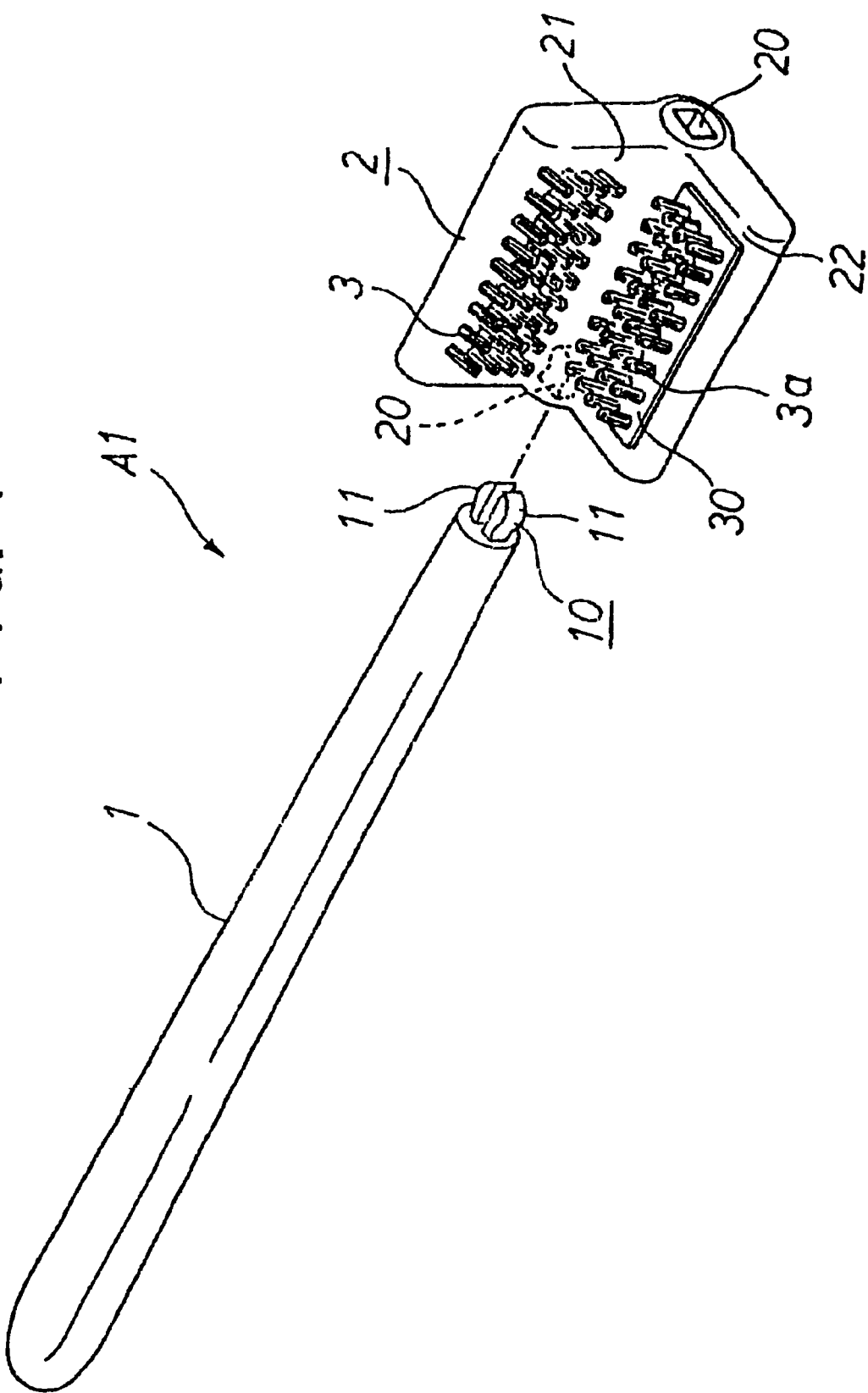
FIG. 1 is an exploded perspective view of a toothbrush according to an embodiment of the present invention.

First through third inventions will be described in detail below based on embodiments shown in the drawings.

Figure 2:
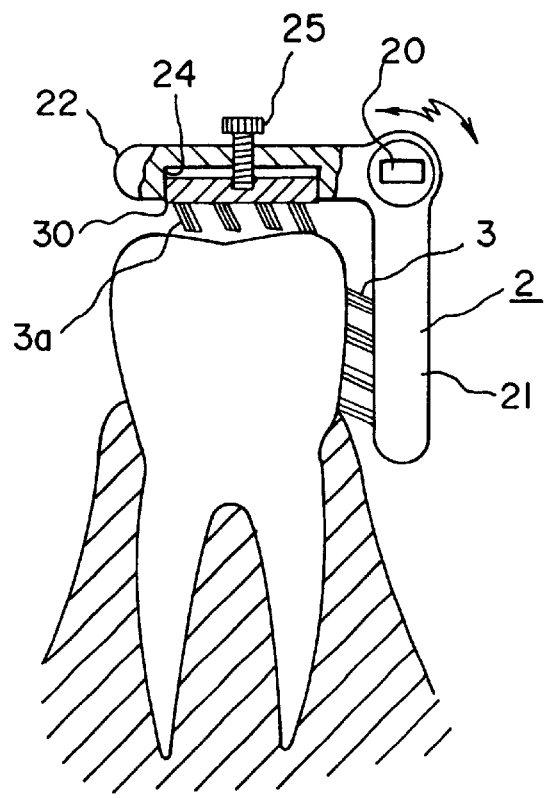
FIG. 2 is a view illustrative of the structure and operation of bristle assemblies of the toothbrush.
Figure 3:
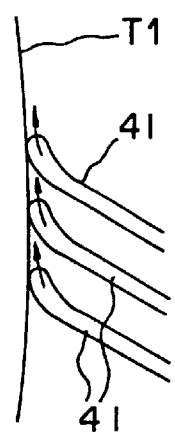
FIG. 3 is an enlarged view of tip ends of bristles.

FIG. 1 is an exploded perspective view of a toothbrush according to an embodiment of the present invention. FIG. 2 is a view illustrative of the structure and operation of bristle assemblies of the toothbrush. FIG. 3 is an enlarged view of tip ends of bristles.

A toothbrush A1 which is manually operable in use comprises a grip handle 1, a crown cap 2, and bristle assemblies 3, 3a.

The grip handle 1 is in the form of a rod of plastic and has an engaging body 10 as a mounting means on its distal end. The engaging body 10 comprises a pair of juxtaposed flexible members 11 spaced from each other and each composed of an engaging member having a curved outer side projecting outwardly.

The crown cap 2 comprises a member made of plastic and having a predetermined length, and has a substantially L-shaped cross section. The crown cap 2 has a vertical wing 21 for covering a tooth side and a horizontal wing 22 for covering an occlusal tooth area. The crown cap 2 has a pair of engaging holes 20 (one shown in FIG. 2) defined in the respective corners of longitudinal ends thereof, each of the engaging holes 20 serving as part of the mounting means for receiving the engaging body 10. The engaging body 10 can easily engage in and disengage from one of the engaging holes 20 with small forces, and can be fixed in position when engaging in one of the engaging holes 20.

The bristle assemblies 3, 3a are mounted on respective inner surfaces of the vertical and horizontal wings 21, 22 of the crown cap 2. The bristle assemblies 3 on the vertical wing 21 are directly planted on the inner surface thereof such that their distal ends are inclined at an angle of substantially 45° toward the bent corner of the crown cap 2.

As shown in FIG. 2, the bristle assembly 3a on the horizontal wing 22 is mounted on its inner surface such that the projection of the bristle assembly 3a from the inner surface of the horizontal wing 22 can be adjusted in a certain range by an adjusting means. The adjusting means comprises a bristle base 30 in the form of an elongate rectangular plate. The bristle base 30 is disposed in a rectangular guide hole 24 defined in the horizontal wing 22 for sliding movement into and out of the guide hole 24. An adjustment screw 25 threaded through a ceiling of the guide hole 24 has a tip end rotatably mounted in a central area of an inner wall of the bristle base 30. When the adjustment screw 25 is turned, the bristle base 30 slides into or out of the guide hole 24, thereby adjusting the projection of the bristle assembly 3a in a certain range.

As with the bristle assembly 3, the bristle assembly 3a is planted on the bristle base 30 such that their distal ends are inclined at an angle of substantially 45° toward the bent corner of the crown cap 2.

As shown in FIG. 3, the bristle assemblies 3, 3a have bristles 41 whose tip ends are bent toward the bent corner of the crown cap 2 and are rounded. The bristles 41 thus shaped are sufficiently effective to remove plaque off teeth without damaging the gum when they brush the teeth.

A process of using the toothbrush according to this embodiment and operation thereof will be described below with reference to FIGS. 1 through 3.

(1) The length of tooth crowns which project from the gum varies from individual to individual. To use the toothbrush, the following adjustments are made in order to accommodate individuals' differences.

First, the tip end of the adjustable bristle assembly 3a is held against the occlusal tooth areas, and the projection of the bristle assembly 3a is adjusted by turning the adjustment screw 25 so that the other bristle assembly 3 abuts reliably against the boundaries (tooth necks) between the tooth sides and the gum.

(2) The tip end of the bristle assembly 3a is held against the occlusal tooth areas, and the tip end of the bristle assembly 3 is held against the tooth sides and the gum, followed by manual reciprocating swinging movement of the grip handle 1 about its own axis.

Though the bristle assemblies 3, 3a are angularly moved back and forth at this time, since the tip ends of the bristle assemblies 3, 3a are inclined toward the bent corner of the crown cap 2, the frictional force is stronger upon angular movement toward the bent corner of the crown cap 2, and weaker upon angular movement in the opposite direction. Therefore, plaque, tartar, and calculus deposited on the occlusal tooth areas, the tooth sides, and the tooth necks are gathered toward the bent corner of the crown cap 2 on its inner surface. For the same reason, the gum is not peeled off the tooth necks, and plaque, tartar, and calculus deposited on the tooth necks are removed without being pushed between the teeth and the gum.

(3) When the brushing of tooth regions which can be brushed in one direction by the crown cap 2 is finished, the crown cap 2 is removed from the grip handle 1, and the engaging body 10 of the grip handle 1 is caused to engage in the opposite engaging hole 20 of the crown cap 2. The vertical and horizontal wings 21, 22 of the crown cap 2 are now switched around, allowing the toothbrush to brush other tooth regions that have not been brushed.

Specifically, if the crown cap 2 and the grip handle 1 are assembled as shown in FIG. 1, then it is possible for the toothbrush to brush the outer surfaces of teeth on the lower jaw ranging from left back teeth to front teeth, and the inner surfaces of teeth on the lower jaw ranging from right back to front teeth, and also to brush the inner surfaces of teeth on the upper jaw ranging from left back to front teeth and the outer surfaces of teeth on the upper jaw ranging from right back to front teeth.

If the crown cap 2 is mounted in the opposite direction on the grip handle 1, then it is possible for the toothbrush to brush the outer surfaces of teeth on the lower jaw ranging from right back teeth to front teeth, and the inner surfaces of teeth on the lower jaw ranging from left back to front teeth, and also to brush the inner surfaces of teeth on the upper jaw ranging from right back to front teeth and the outer surfaces of teeth on the upper jaw ranging from left back to front teeth.

Figure 4:
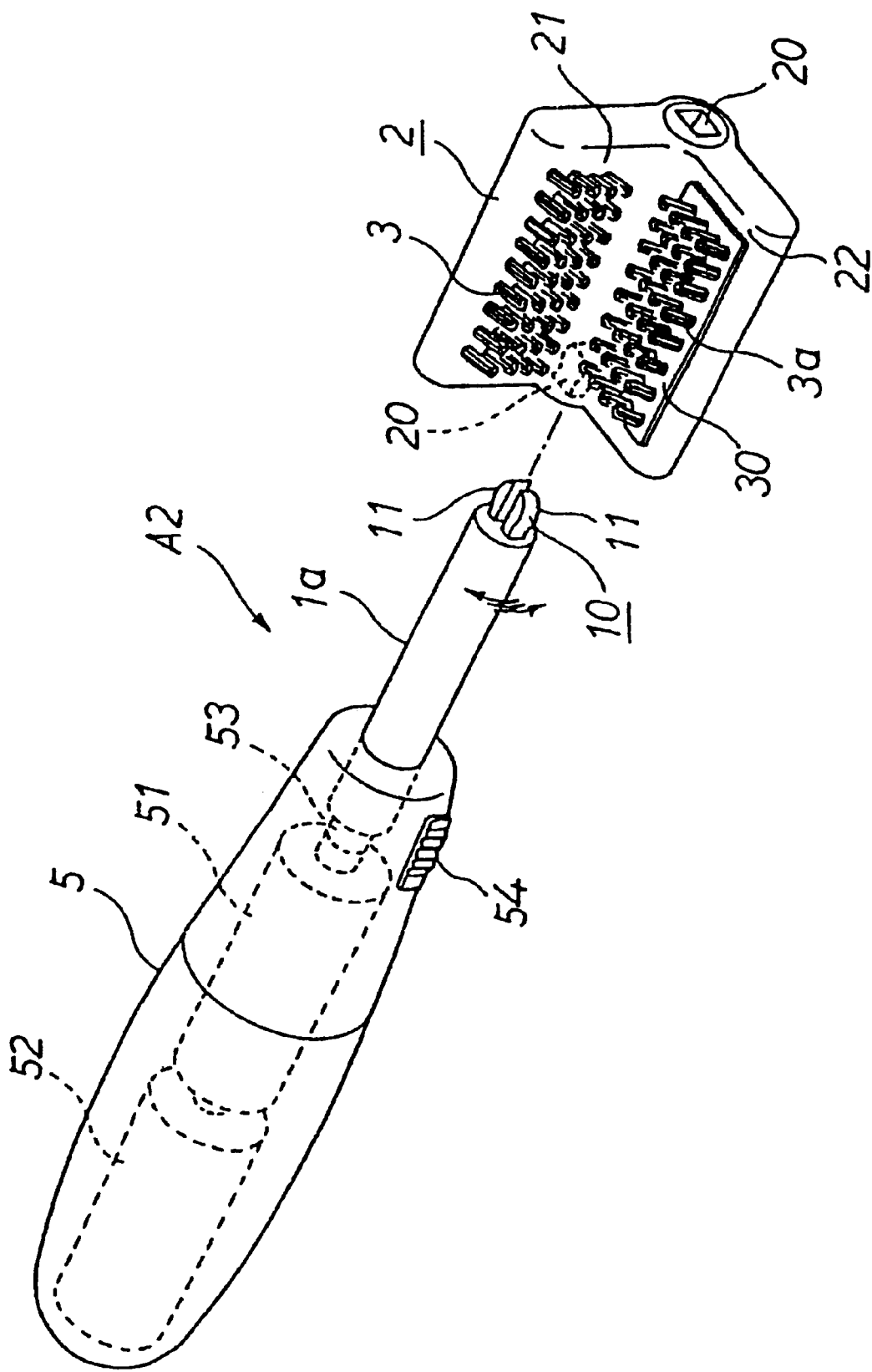
FIG. 4 is an exploded perspective view of an electric toothbrush according to the present invention.

FIG. 4 is an exploded perspective view of an electric toothbrush according to the present invention.

An electric toothbrush A2 has a grip base 5 including a handle 1a on its distal end. The handle 1a can be actuated by a motor 51 housed as an electric actuator means in the grip base 5, to angularly move back and forth about its own axis through a converter mechanism 53. The converter mechanism 53 is of a known structure, and will not be described in detail.

In this embodiment, the handle 1a only moves angularly back and forth about its own axis. However, it is possible for the handle 1a to switch to back-and-forth sliding movement in the axial direction. A battery 52 is also housed in the grip base 5 and a switch 54 is mounted on the grip base 5.

The structure of the distal end of the handle 1a and the structures of a crown cap 2 and bristle assemblies 3, 3a mounted on the handle 1a are the same as those of the toothbrush A1 described above, and will not be described in detail. Those parts of the electric toothbrush A2 which are identical or equivalent to those of the toothbrush A1 are denoted by identical reference numerals.

A method of using the electric toothbrush A2 and operation thereof are substantially the same as those of the toothbrush A1 except that the bristle assemblies 3, 3a are angularly moved back and forth by electric energy for higher efficiency.

Figure 5:
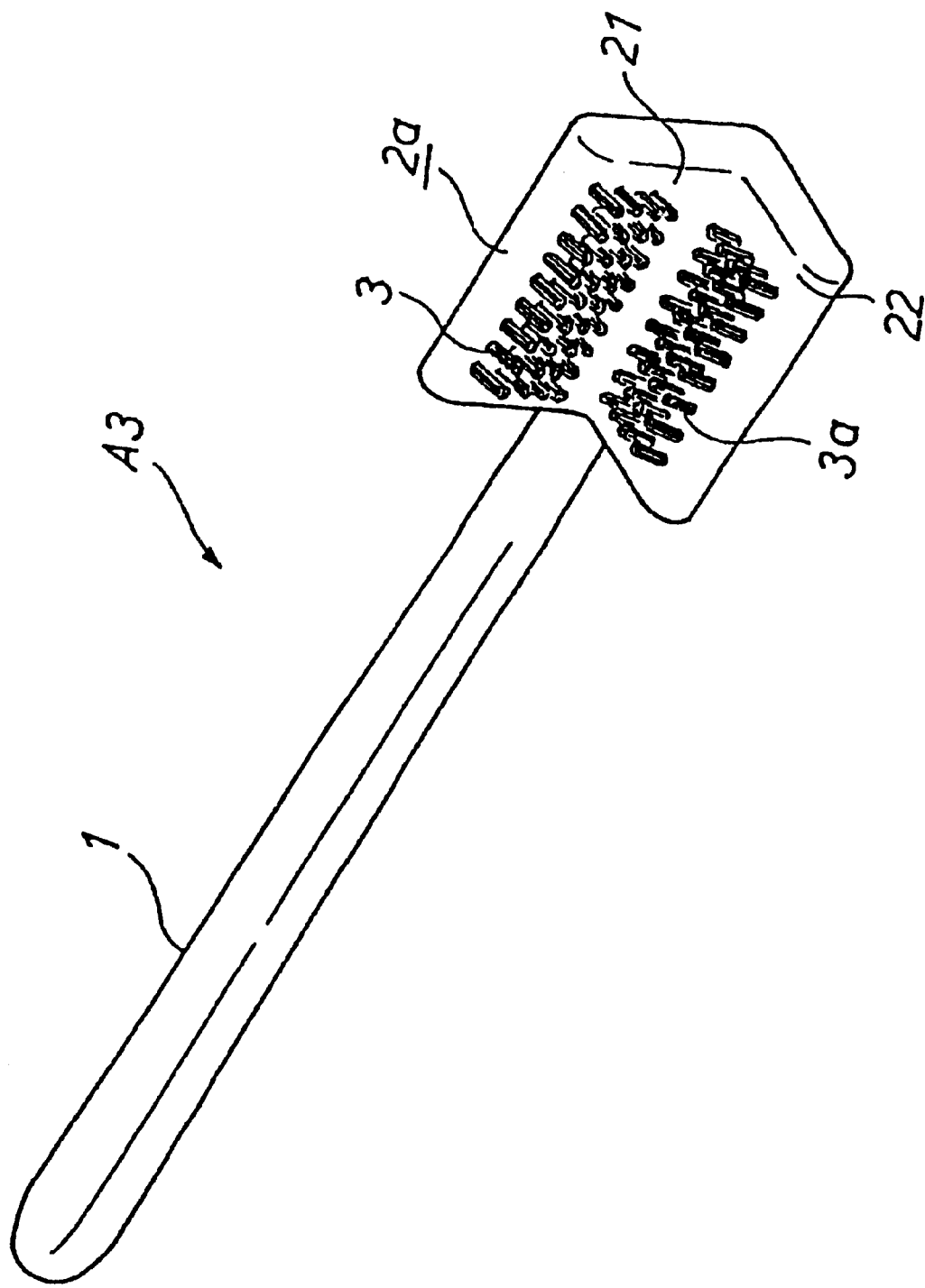
FIG. 5 is a perspective view of a toothbrush according to another embodiment of the present invention.

FIG. 5 is a perspective view of a toothbrush according to another embodiment of the present invention.

A toothbrush A3 which is manually operable in use in the same manner as with the toothbrush A1. The toothbrush A3 is structurally different from the toothbrush A1 in that a grip handle 1 is fixed to an end of a crown cap 2a, and a bristle assembly 3a is directly planted on a horizontal wing 22 without the brush base 30, etc. used as adjusting means.

The structure of other portions of the toothbrush A3 is the same as that of the toothbrush A1, and will not be described in detail. Those parts of the toothbrush A3 which are identical or equivalent to those of the toothbrush A1 are denoted by identical reference numerals.

A process of using the toothbrush A3 and operation thereof are substantially the same as those of the toothbrush A1. However, the toothbrush A3 has no adjusting means for bristle assemblies unlike the toothbrush A1, and the projection of the bristle assemblies cannot be adjusted. Since the wings of the crown cap 2a are structurally identical to each other, the toothbrush A3 has no particular orientation, and can be used more conveniently as the crown cap 2a does not need to be changed in direction.

Fourth through seventh inventions will be described in detail below based on embodiments shown in the drawings.

Figure 6:
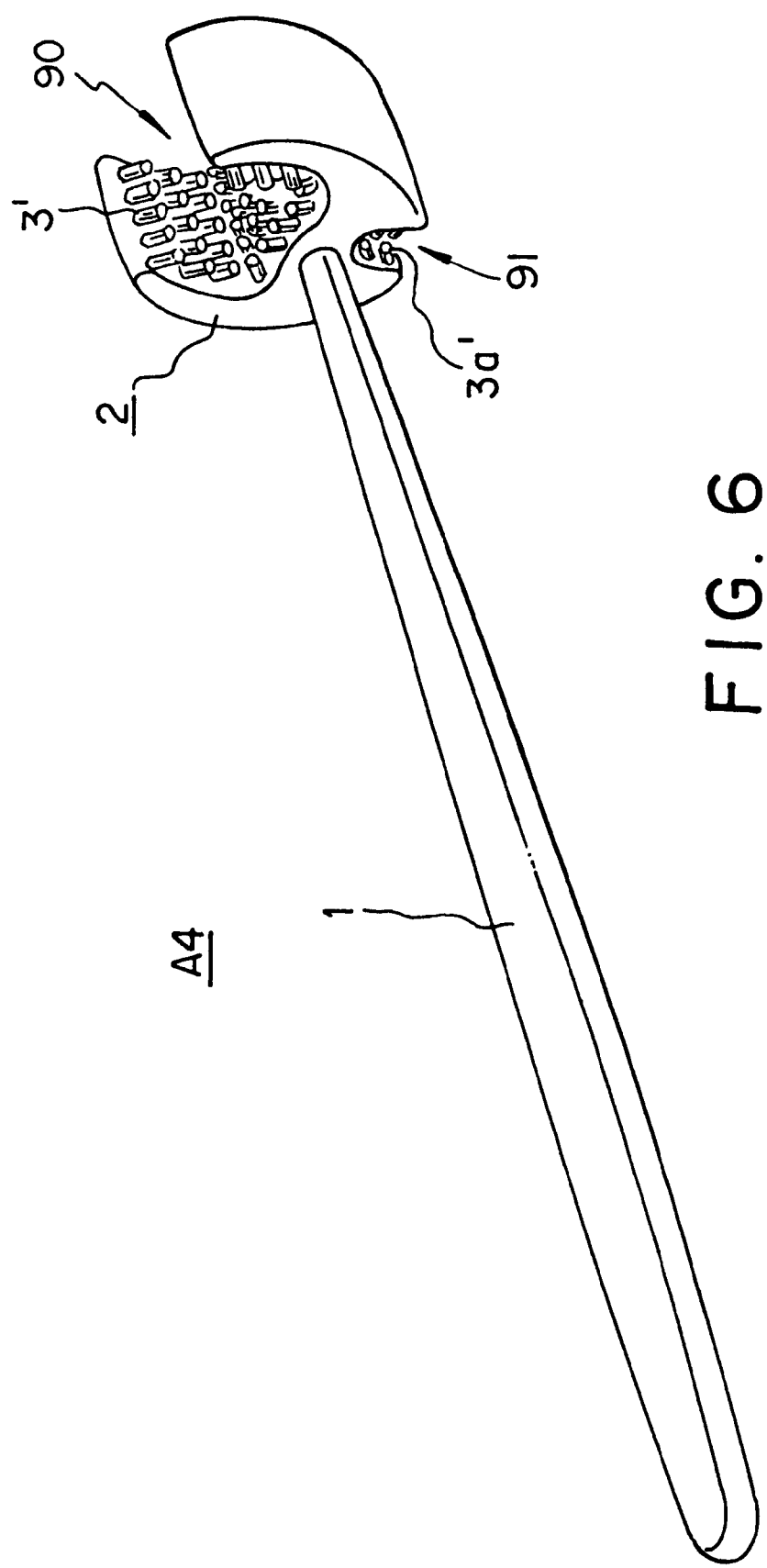
FIG. 6 is a perspective view of a toothbrush according to an embodiment of the present invention.
Figure 7:
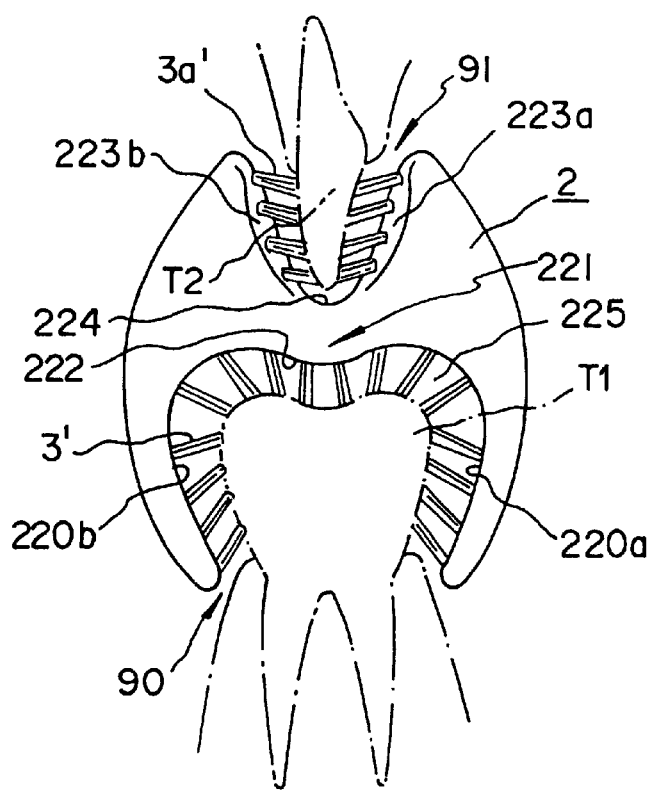
FIG. 7 is a view illustrative of the structure of bristle assemblies and the manner in which the bristle assemblies abut against tooth surfaces.
Figure 8:
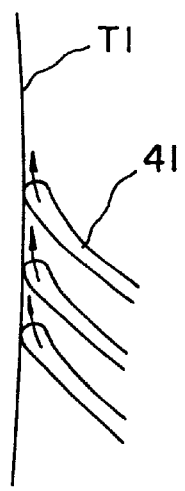
FIG. 8 is an enlarged view of tip ends of bristles.

FIG. 6 is a perspective view of a toothbrush according to an embodiment of the present invention. FIG. 7 is a view illustrative of the structure of bristle assemblies and the manner in which the bristle assemblies abut against tooth surfaces. FIG. 8 is an enlarged view of tip ends of bristles.

A toothbrush A4 which is manually operable in use comprises a grip handle 1 and a crown cap 2. The grip handle 1 is in the form of a rod of plastic and the crown cap 2 is fixed to a distal end of the grip handle 1.

The crown cap 2 is molded of plastic and has a molar tooth fitting portion 90 having a substantially heart-shaped cross section and a front tooth fitting portion 91 having a substantially V-shaped cross section. The front tooth fitting portion 91 is of a curved shape such that its central region is slightly narrow as viewed in plan. The crown cap 2 has a round outer profile for protecting the inside of a mouth when in use.

A bristle assembly 3' is planted on the inner surface of the molar tooth fitting portion 90 substantially in its entirety such that the bristle assembly 3' is inclined at an angle of substantially 45° to surfaces of molar teeth to be fitted in the molar tooth fitting portion 90.

Furthermore, a bristle assembly 3a' is planted on the inner surface of the front tooth fitting portion 91 substantially in its entirety such that the bristle assembly 3a' is inclined at an angle of substantially 45° to surfaces of front teeth to be fitted in the front tooth fitting portion 91.

As shown in FIG. 8, the bristle assemblies 3', 3a' have bristles 41 whose tip ends are bent toward the bent corner of the crown cap 2 and are rounded. The bristles 41 thus shaped are sufficiently effective to remove plaque off teeth without damaging the gum when they brush the teeth.

A process of using the toothbrush according to this embodiment and operation thereof will be described below with reference to FIGS. 6 through 8.

(1) The molar tooth fitting portion 90 is fitted over a molar tooth T1 and the bristle assembly 3' are directed substantially at 45° with respect to surfaces of the molar tooth T1. Then, the grip handle 1 is manually angularly moved back and forth around its own axis or in the direction of the tooth axis or the direction normal thereto for thereby brushing the molar tooth T1.

Though the bristle assemblies 3', 3a' are angularly moved back and forth at this time, since the bristle assemblies 3', 3a' are inclined to the tooth surfaces, the frictional force is stronger upon movement toward the tip end of the tooth, and weaker upon movement in the opposite direction. Therefore, plaque, tartar, and calculus deposited on the occlusal tooth area, the tooth sides, and the tooth neck of the molar tooth T1 are gathered toward the center of the molar tooth fitting portion 90. For the same reason, the gum is not peeled off the tooth neck, and plaque, tartar, and calculus deposited on the tooth neck are removed without being pushed between the tooth and the gum.

(2) When the brushing of the molar tooth T1 is finished, the front tooth fitting portion 91 is fitted over a front tooth T2. Upon brushing the front tooth T2 in the same manner as with the molar tooth T1, plaque, tartar, and calculus are gathered toward the center of the front tooth fitting portion 91, and removed without being pushed between the tooth and the gum.

Figure 9:
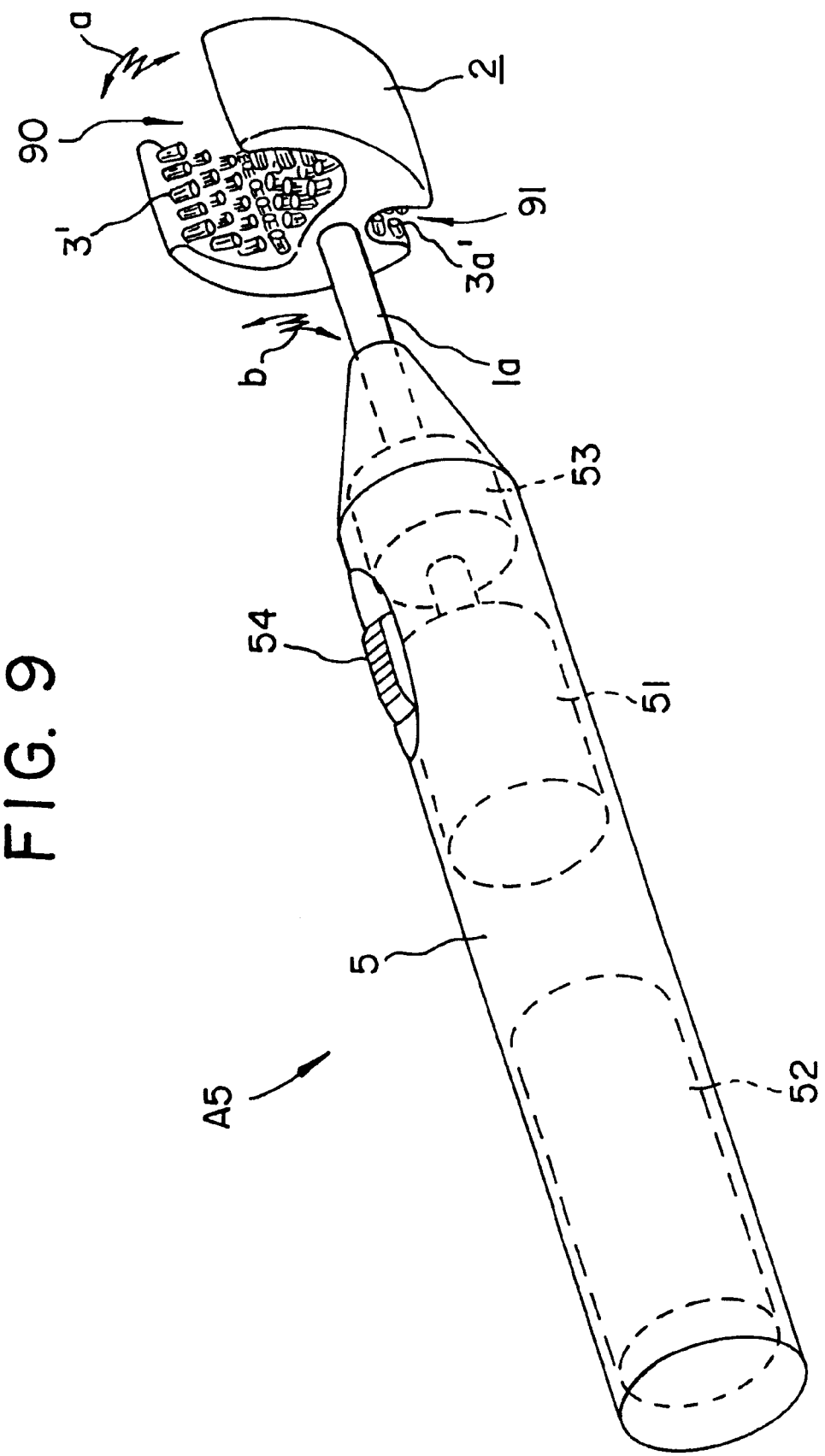
FIG. 9 is a perspective view of an electric toothbrush according to the present invention.

FIG. 9 is a perspective view of an electric toothbrush according to the present invention.

An electric toothbrush A5 has a grip base 5 including a handle 1a on its distal end.

The handle 1a can be actuated by a motor 51 housed as an electric actuator means in the grip base 5, to angularly move back and forth about its own axis (as indicated by the arrows "a") and in the direction of the tooth axis (as indicated by arrows "b") through a converter mechanism 53. The converter mechanism 53 is of a known structure, and will not be described in detail.

In this embodiment, it is possible for the handle 1a to switch in its movement between the direction around its own axis, the direction of the tooth axis, and the direction normal thereto with a selector switch (not shown). A battery 52 is also housed in the grip base 5 and a switch 54 is mounted on the grip base 5.

The structures of a crown cap 2 and bristle assemblies 3', 3a' fixed to the distal end of the handle 1a are the same as those of the toothbrush A4 described above, and will not be described in detail. Those parts of the electric toothbrush A5 which are identical or equivalent to those of the toothbrush A4 are denoted by identical reference numerals.

A method of using the electric toothbrush A5 and operation thereof are substantially the same as those of the toothbrush A4 except that the bristle assemblies 3', 3a' are angularly moved back and forth by electric energy for higher efficiency.

Figure 10:
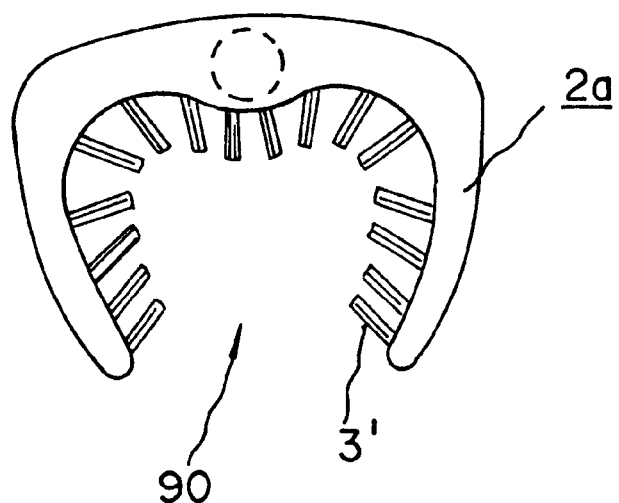
FIG. 10 is a front elevational view of the structure of another crown cap.
Figure 11:
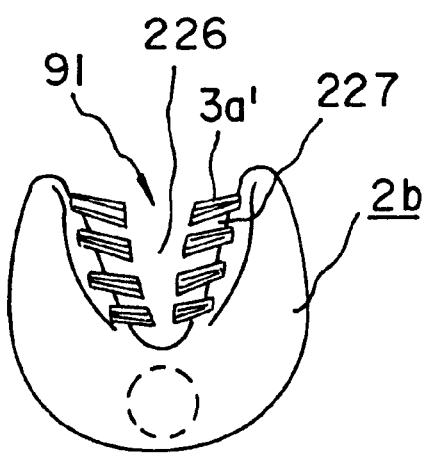
FIG. 11 is a front elevational view of the structure of still another crown cap.

FIGS. 10 and 11 are front elevational views showing other structures of crown caps.

A crown cap 2a shown in FIG. 10 is of a structure having a molar tooth fitting portion 90 and bristle assembly 3', only, and is used solely for brushing molar teeth.

A crown cap 2b shown in FIG. 11 is of a structure having a front tooth fitting portion 91 and bristle assembly 3a' only, and is used solely for brushing front teeth.

Those parts of the crown caps 2a, 2b shown in FIGS. 10 and 11 which are identical or equivalent to those of the crown cap 2 are indicated by identical reference numerals.

While the crown caps 2a, 2b operate substantially in the same manner as the crown cap 2 according to the above embodiment, the crown caps 2a, 2b are simpler in structure and smaller in size, and hence can be moved easily in the mouth.

Eighteenth and nineteenth inventions will be described in detail below based on embodiments shown in the drawings.

Figure 12:
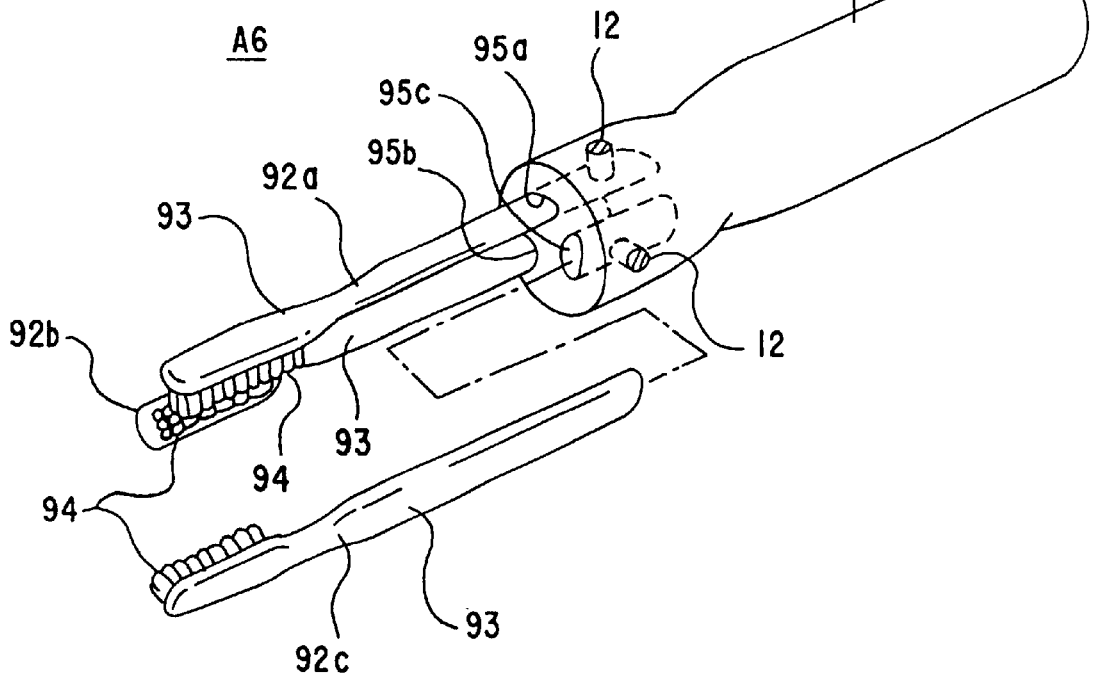
FIG. 12 is an exploded perspective view of a toothbrush according to an embodiment of the present invention.
Figure 13:
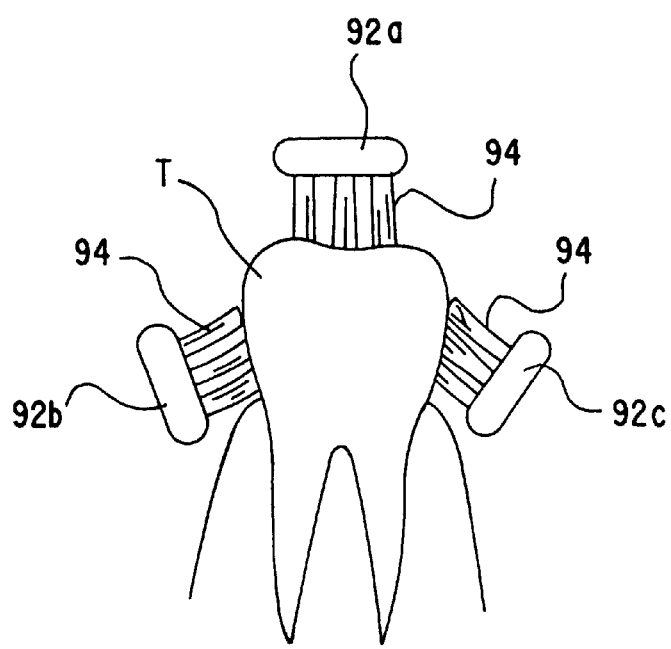
FIG. 13 is a view illustrative of the structure of bristle assemblies and the manner in which the bristle assemblies abut against tooth surfaces.
Figure 14:
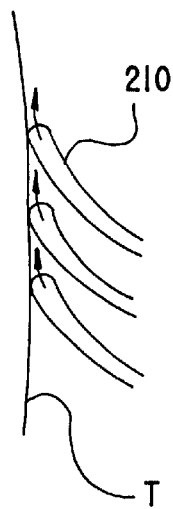
FIG. 14 is an enlarged view of tip ends of bristles.

FIG. 12 is an exploded perspective view of a toothbrush according to an embodiment of the present invention. FIG. 13 is a view illustrative of the structure of bristle assemblies and the manner in which the bristle assemblies abut against tooth surfaces. FIG. 14 is an enlarged view of tip ends of bristles.

A toothbrush A6 which is manually operable in use comprises a grip handle 1 and three toothbrush bodies 92a, 92*b*, 92*c*. The grip handle 1 is in the form of a rod of plastic and the toothbrush bodies 92*a*, 92*b*, 92*c* are detachably mounted on a distal end of the grip handle 1.

Each of the toothbrush bodies 92*a*, 92*b*, 92*c* has a handle 93 with bristle assemblies 94 mounted on its distal end portion which have a round profile for protecting the inside the mouth from damage during use.

The structure by which the toothbrush bodies 92*a*, 92*b*, 92*c* are attached to the grip handle 1 will be described below. The distal end of the grip handle 1 has three fixing holes 95*a*, 95*b*, 95*c* defined therein and three threaded holes also defined therein between the fixing holes 95*a*, 95*b*, 95*c* and an outer surface of the grip handle 1. Fastening screws 12 are threaded in the respective threaded holes. When the fastening screws 12 are tightened, the respective ends of the handles 93 of the toothbrush bodies 92*a*, 92*b*, 92*c* that are received in the fixing holes 95*a*, 95*b*, 95C are secured therein.

The fixing holes 95*a*, 95*b*, 95*c* have a substantially elliptical cross section similar to that of the handles 93, so that when the handles are inserted into the respective fixing holes 95*a*, 95*b*, 95*c*, the angles of the toothbrush bodies 92*a*, 92*b*, 92*c* about their own axes are automatically set.

The angles to which the toothbrush bodies 92*a*, 92*b*, 92*c* are set will be described below with reference to FIG. 13.

The toothbrush body 92*a* corresponds to the occlusal tooth area of a tooth, and its bristle assemblies 94 abut against the occlusal tooth area substantially perpendicularly thereto. The toothbrush bodies 92*b*, 92*c* correspond respectively to the opposite sides of the tooth. The bristle assemblies 94 of the toothbrush bodies 92*b*, 92*c* are inclined at an angle of substantially 45° to the tooth sides toward the tip end of the tooth which is to be fitted in a region surrounded by these bristle assemblies 94.

As shown in FIG. 14, the bristle assemblies 94 have bristle fibers 210 whose tip ends are bent toward the tip end of a tooth and are rounded. The bristle fibers 210 thus shaped are sufficiently effective to remove plaque off teeth without damaging the gum when they brush the teeth.

A process of using the toothbrush according to this embodiment and operation thereof will be described below with reference to FIG. 12 through 14.

A tooth T is fitted into the space surrounded by the bristle assemblies 94, and the bristle assemblies 94 corresponding to the sides of the tooth are directed substantially at 45° with respect to the tooth sides. Then, the grip handle 1 is manually vibrated around its own axis or in the direction of the tooth axis or the direction normal thereto for thereby brushing the tooth.

Though the bristle assemblies 94 are vibrated at this time, since the bristle assemblies 94 are inclined to the tooth sides, the frictional force is stronger upon movement toward the tip end of the tooth, and weaker upon movement toward the roots of the tooth. Therefore, plaque, tartar, and calculus deposited on the occlusal tooth area, the tooth sides, and the tooth neck of the tooth are gathered toward the center of the tip end of the tooth. For the same reason, even when rubbed by the bristle assemblies 94, the gum is not peeled off the tooth neck, and plaque, tartar, and calculus deposited on the tooth neck are removed without being pushed between the tooth and the gum.

FIG. 15 is a perspective view of an electric toothbrush according to the present invention.

An electric toothbrush A7 has a grip base 5 including an attachment 96 on its distal end. To the attachment 96, there are attached three toothbrush bodies 92*a*, 92*b*, 92*c* as with the toothbrush A6.

The attachment 96 can be actuated by a motor 51 housed as an electric actuator means in the grip base 5, to angularly move back and forth about its own axis (as indicated by the arrows "a") and in the direction of the tooth axis (as indicated by arrows "b") through a converter mechanism 53. The converter mechanism 53 is of a known structure, and will not be described in detail.

In this embodiment, it is possible for the attachment 96 (handles 93) to switch in its movement between the direction around its own axis and the direction of the tooth axis with a selector switch 54. In addition, the attachment 96 may be vibrated in the direction normal to the direction of the tooth axis (i.e., vibrated in the direction in which the attachment 96 moves into and out of the mouth). A battery 52 is housed in the grip base 5.

Those parts of the electric toothbrush A7 which are identical or equivalent to those of the toothbrush A6 are denoted by identical reference numerals.

A method of using the electric toothbrush A7 and operation thereof are substantially the same as those of the toothbrush A6 except that the toothbrush bodies 92*a*, 92*b*, 92*c* (the bristle assemblies 94) are vibrated by electric energy for higher efficiency.

FIG. 16 is an exploded perspective view of an electric toothbrush according to another embodiment of the present invention.

An electric toothbrush A8 has three handles 56*a*, 56*b*, 56*c* mounted on an attachment 96*a*. The handles 56*a*, 56*b*, 56*c* can be vibrated about their own axes independently by a converter mechanism 53. The handles 56*a*, 56*b*, 56*c* have respective fitting portions 57 of square-shaped cross section on their distal ends.

Toothbrush bodies 92*a*1, 92*b*1, 92*c*1 are detachably mounted on the respective fitting portions 57. The toothbrush bodies 92*a*1, 92*b*1, 92*c*1 include respective handles 93 which have in their proximal ends respective fitting holes 201 that receive the respective fitting portions 57 fitted therein. The fitting portions 57 can detachably be fitted in the fitting holes 201 by known means in one operation.

The angles at which the toothbrush bodies 92*a*1, 92*b*1, 92*c*1 are attached around the axis of the toothbrush are set in the same manner as with the above embodiments.

Those parts of the electric toothbrush A8 which are identical or equivalent to those of the electric toothbrush A7 are indicated by identical reference numerals.

A method of using the electric toothbrush A8 and operation thereof are essentially the same as with the electric toothbrush A7 except that the toothbrush bodies 92*a*1, 92*b*1, 92*c*1 can be detached and attached with ease and the toothbrush bodies 92*a*1, 92*b*1, 92*c*1 (the bristle assemblies 94) can be vibrated about their respective axes by electric energy.

Figure 17:
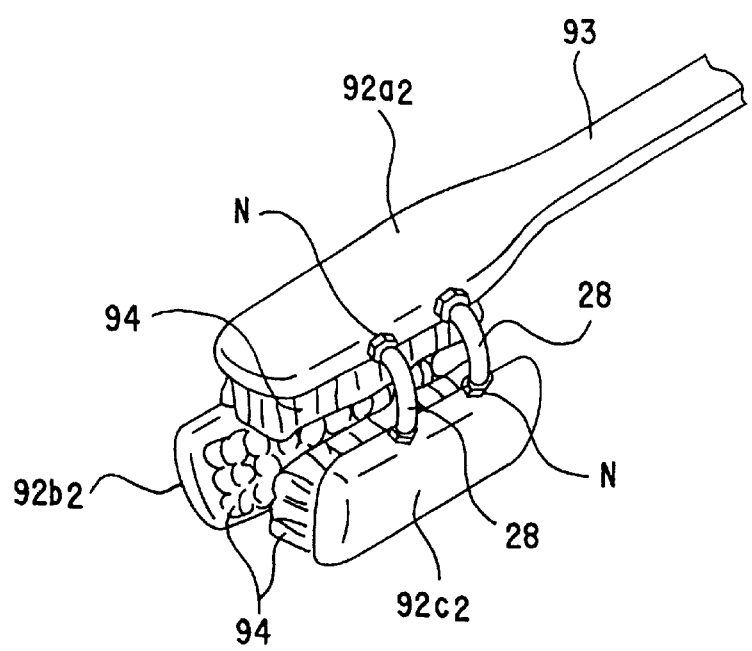
FIG. 17 is a fragmentary perspective view of toothbrush bodies according to a second embodiment of the present invention.

FIG. 17 is a fragmentary perspective view of toothbrush bodies according to a second embodiment: of the present invention.

In this embodiment, only a toothbrush body 92*a*2 has a handle 20, and toothbrush bodies 92*b*2, 92*c*2 which are of substantially the same extent as bristle assemblies are attached to the toothbrush body 92*a*2 by curved arm pins 28 of stainless steel that are disposed on opposite sides of the toothbrush body 92*a*2. The arm pins 28 are secured in position by nuts N that are tightened. When loosened, the nuts N allow only the toothbrush bodies 92*b*2, 92*c*2 to be replaced.

The angles at which the toothbrush bodies 92a2, 92b2, 92c2 are attached around the axis of the toothbrush are set in the same manner as with the above embodiments.

Figure 18:
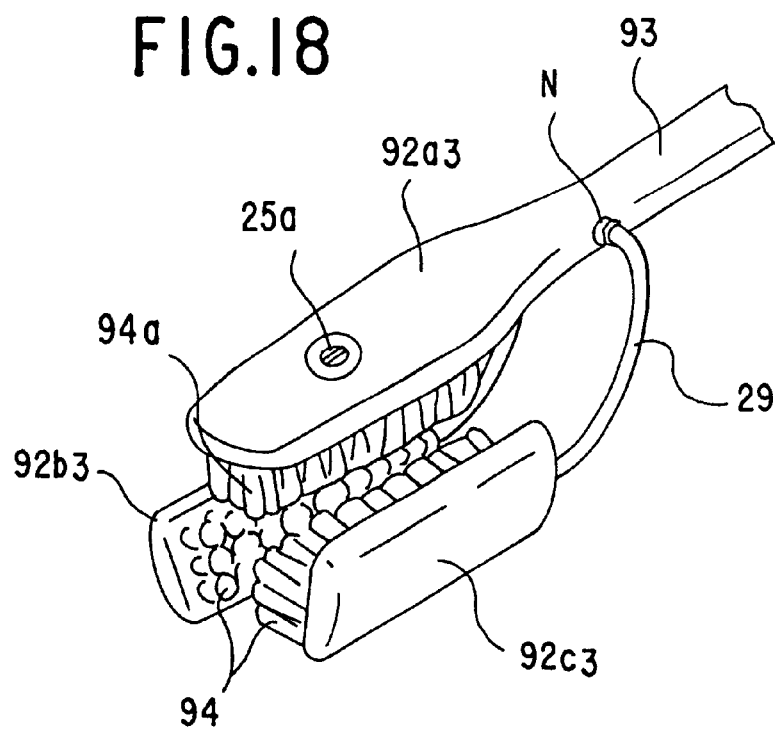
FIG. 18 is a fragmentary perspective view of toothbrush bodies according to a third embodiment of the present invention.
Figure 19:
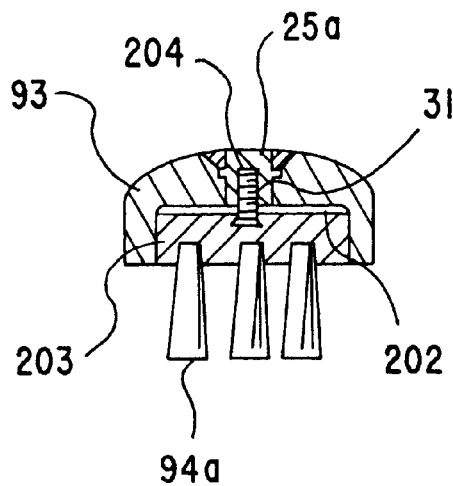
FIG. 19 is a cross-sectional view of one of the toothbrush bodies according to the third embodiment of the present invention.

FIG. 18 is a fragmentary perspective view of toothbrush bodies according to a third embodiment of the present invention, and FIG. 19 is a cross-sectional view of one of the toothbrush bodies according to the third embodiment.

In this embodiment, toothbrush bodies 92b 3, 92c3 are attached to a toothbrush body 92a3 by arm pins 29 extending from the neck of a handle 20 of the toothbrush body 92a3.

As shown in FIG. 19, an adjustment screw 25a is undetachably rotatably mounted on an upper surface of the handle 93 near its distal end. The adjustment screw 25a has a threaded hole 31 defined in its lower portion.

The handle 93 has a recess 202 defined in a lower portion thereof near its distal end and housing a vertically movable body 203. A screw 204 is vertically fixed to an upper surface of the vertically movable body 203, and threaded in the threaded hole 31. A bristle assembly 94a is mounted on a lower surface of the vertically movable body 203.

When the adjustment screw 25a is turned, the vertically movable body 203 is vertically moved to adjust the height of the bristle assembly 94a of the toothbrush body 92a3 for use.

The angles at which the toothbrush bodies 92a3, 92b3, 92c3 are attached around the axis of the toothbrush are set in the same manner as with the above embodiments.

Figure 20:
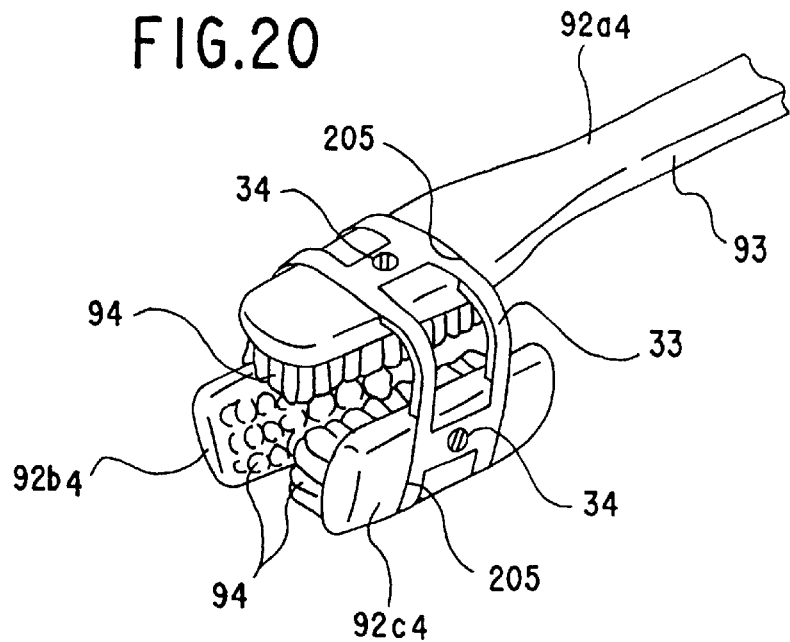
FIG. 20 is a fragmentary perspective view of toothbrush bodies according to a fourth embodiment of the present invention.

FIG. 20 is a fragmentary perspective view of toothbrush bodies according to a fourth embodiment of the present invention.

In this embodiment, toothbrush bodies 92a4, 92b4, 92c4 have fitting grooves 205 defined in their respective outer surfaces, and joints 33 of stainless steel having a channel shape in front elevation are fitted in the fitting grooves 205. The joints 33 are secured in position to the toothbrush bodies 92a4, 92b4, 92c4, thus integrally joining the toothbrush bodies 92a4, 92b4, 92c4 to each other.

The angles at which the toothbrush bodies 92a4, 92b4, 92c4 are attached around the axis of the toothbrush are set in the same manner as with the above embodiments.

Figure 21:
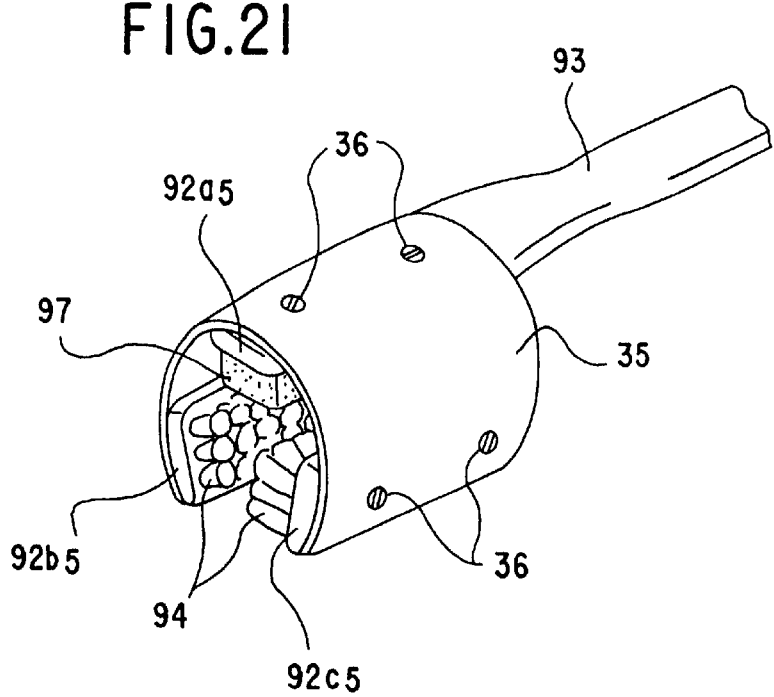
FIG. 21 is a fragmentary perspective view of toothbrush bodies according to a fifth embodiment of the present invention.

FIG. 21 is a fragmentary perspective view of toothbrush bodies according to a fifth embodiment of the present invention.

In this embodiment, toothbrush bodies 92a5, 92b5, 92c5 are integrally joined to each other by a curved enclosing plate 35 of stainless steel which is fastened to them by screws 36. A cushion 97 made of hard sponge, rather than bristle assembly, is attached to a lower surface of the toothbrush body 92a5.

Those parts of the toothbrushes shown in FIGS. 17 through 21 which are identical or equivalent to those of the aforesaid embodiments are indicated by identical reference numerals.

Preferred embodiments of tenth through sixteenth inventions will be described below.

Figure 22:
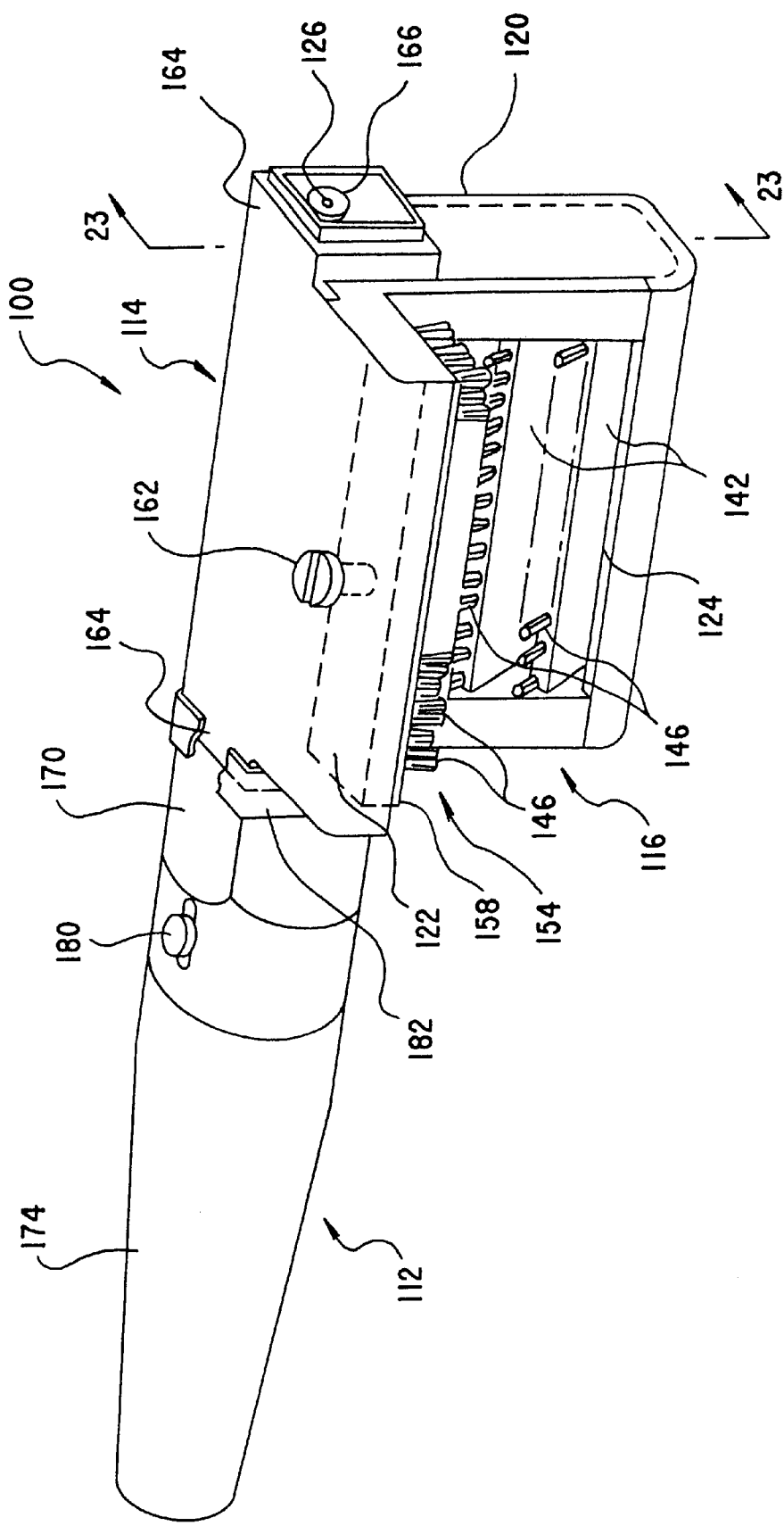
FIG. 22 is a perspective view of an electric toothbrush according to an embodiment of the present invention.
Figure 23:
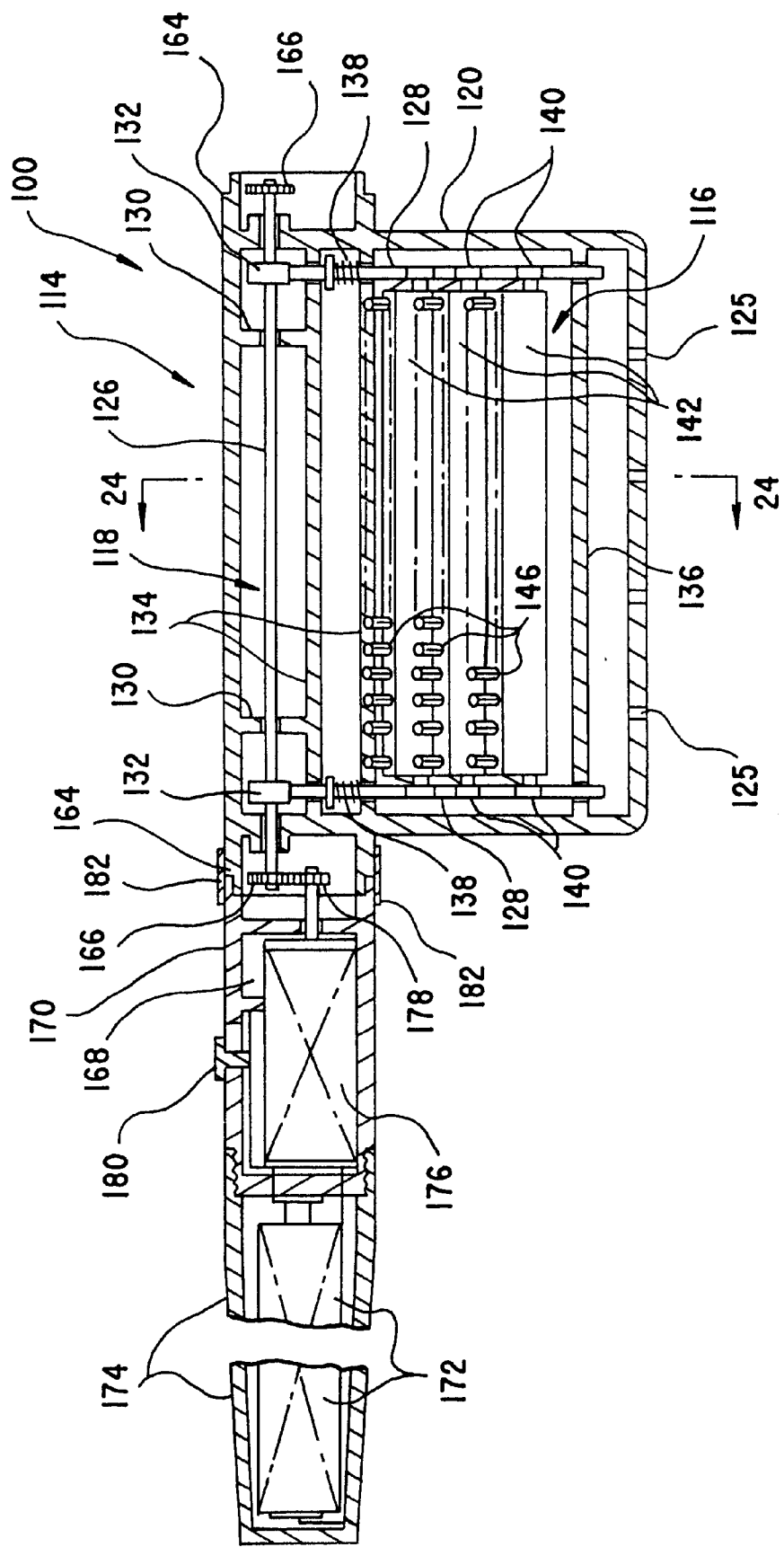
FIG. 23 is a cross-sectional view taken along line 23—23 of FIG. 22.
Figure 24:
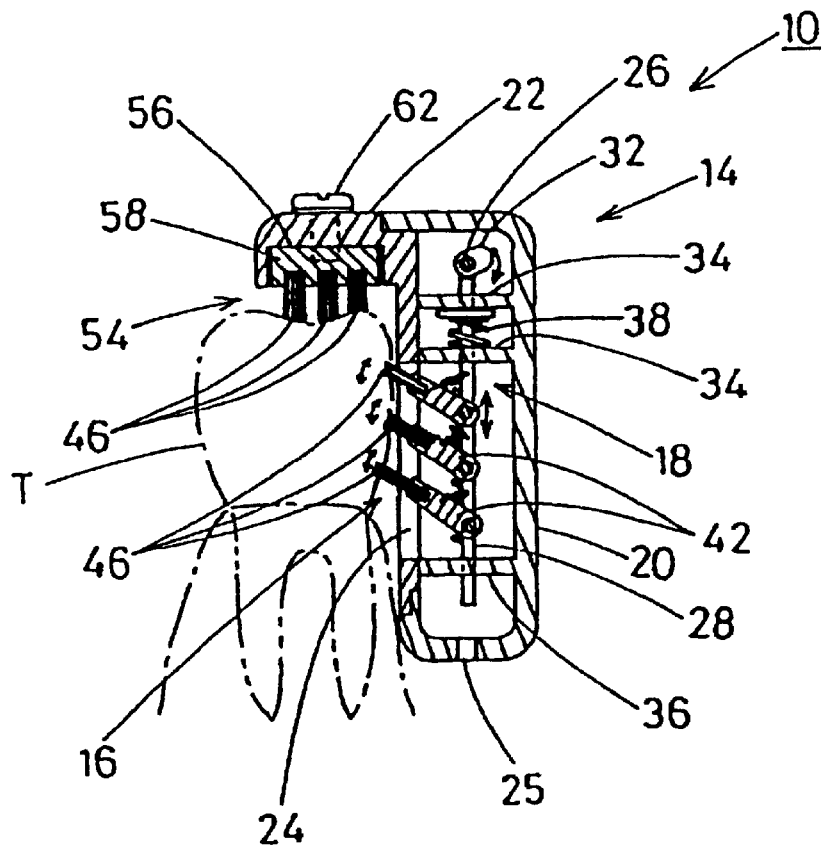
FIG. 24 is a cross-sectional view taken along line 24—24 of FIG. 23.

FIGS. 22, 23, and 24 show an electric toothbrush 100 according to an embodiment of the present invention.

As shown in FIGS. 22, 23, and 24, the electric toothbrush 100 has a casing 114 with a handle 112 projecting from one end thereof. The casing 114 houses a bristle assembly 116 reciprocally angularly movable to swing upwardly along teeth sides while being held against the teeth sides or neighboring regions, and a reciprocally rocking mechanism 118 for reciprocally angularly moving the bristle assembly 116.

As shown in FIGS. 22 and 23, the casing 114 comprises a vertical case 120 on one side and a horizontal case 122 on another side, the cases 120, 122 being joined in an inverted L shape as viewed in end elevation. The horizontal case 122 is joined to the vertical case 120 so as to project from an upper end of the vertical case 120.

The vertical case 120 and the horizontal case 122 are made of a hard synthetic resin or the like. The vertical case 120 has a hole 124 defined in an inner side wall thereof for placing the bristle assembly 116 therein, and a drain hole 125 defined in a bottom wall thereof for draining water out of the casing 114.

As shown in FIGS. 23 and 24, the reciprocally rocking mechanism 118 has a rotatable shaft 126 journaled in an upper position in the vertical case 120, and a pair of swing shafts 128 disposed vertically in the vertical case 120 at respective positions near the ends of the vertical case 120.

The rotatable shaft 126 is rotatably supported by a pair of bearings 130 disposed in the upper position in the vertical case 120. A pair of plate cams 132 is fixedly mounted on the rotatable shaft 126 near its opposite ends and held in sliding contact with the respective upper ends of the swing shafts 128.

The swing shafts 128 are journaled in shaft holes that are defined in two upper bearing plates 134 horizontally disposed in the upper position in the vertical case 120, and shaft holes that are defined in a lower bearing plate 136 horizontally disposed in a lower position in the vertical case 120. Coil springs 138 are mounted on the swing shafts 128, respectively, between the upper bearing plates 134 for normally urging the swing shafts 128 to move upwardly. Pivot supports 140 by which the bristle assembly 116 are pivotally supported are fixedly mounted in upper and lower regions or the swing shafts 128 between the upper and lower bearing plates 134, 136.

When the rotatable shaft 126 of the reciprocally rocking mechanism 118 is rotated, the swing shafts 128 are lowered against the bias of the coil springs 138 each time cam lobes of the plate cams 132 make one revolution, and hence are reciprocally moved in the vertical direction. The reciprocally rocking mechanism 118 is not limited to the rotating plate cams 132, but crank mechanisms or the like may be combined with the rotatable shaft 126 for vertically moving the swing shafts 128 in interlinked relation thereto.

Figure 25:
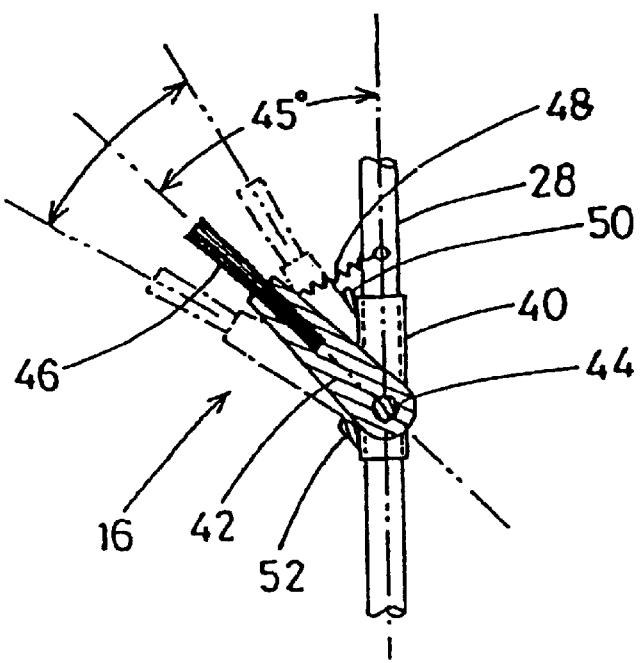
FIG. 25 is an enlarged fragmentary vertical cross-sectional view of a bristle assembly.
Figure 26:
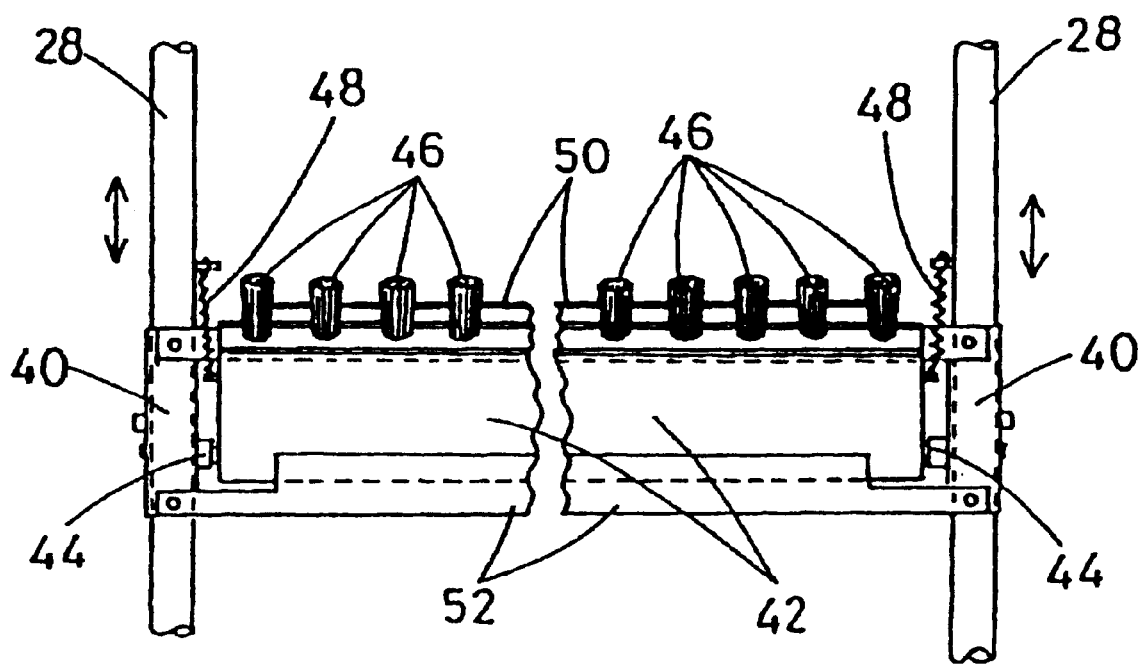
FIG. 26 is an enlarged fragmentary front elevational view of the bristle assembly.

As shown in FIGS. 24, 25, and 26, the bristle assembly 116 have two or three bristle bases 142 positioned in upper and lower positions between the swing shafts 128 of the reciprocally rocking mechanism 118 and extending obliquely upwardly toward the hole 124 defined in the inner side wall of the vertical case 120. Each of the bristle bases 142 is of a flat shape elongate in the horizontal direction and has a support shaft 144 extending longitudinally through and fixed to a lower end thereof. Bristles 146 are planted on an upper end of each of the bristle bases 142.

The bristle bases 142 are pivotally supported by opposite ends of the support shafts 144 on the pivot supports 140 that are fitted over the swing shafts 128 in their upper and lower regions. Resilient members 148 such as coil springs are connected between the opposite ends of the bristle bases 142 and the swing shafts 128. The bristle bases 142 project obliquely upwardly from within the vertical case 120 toward the hole 124 in the inner side wall thereof.

As shown in FIGS. 25 and 26, each of the bristle bases 142 is inclined upwardly at an angle of about 45° from its pivots on the swing shafts 128. Upper and lower stoppers 150, 152 are horizontally mounted on the pivot supports 140 on the swing shafts 128 such that the bristle base 142 can swing vertically in an upward angle of about 15° from the inclined position and in a downward angle of about 15° from the inclined position.

When the bristles 146 on the bristle bases 142 abut against a tooth side and the swing shafts 128 are lowered, the bristle bases 142 are turned upwardly and hence closed until they are engaged by the upper stoppers 150 while being lowered. When the swing shaft 128 are lifted, the bristle bases 142 are spread and received by the lower stoppers 152 while being elevated. On their way upward, the bristle bases 142 are closed under the bias of the resilient members 148 and return to their original position.

Figure 27:
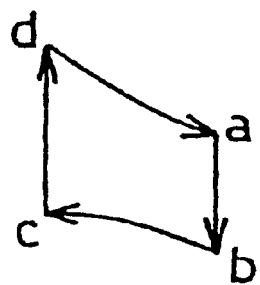
FIG. 27 is a diagram showing paths followed by the tip ends of bristles when the bristle assembly is angularly moved reciprocally.

At this time, the tip ends of the bristles 146 are reciprocally angularly moved upwardly in coaction with the swing shafts 128 along paths as shown in FIG. 27, i.e., a path a–b where the ends of the bristles 146 are lowered and substantially held against a tooth neck, a path b–c where the ends of the bristles 146 abut against the tooth neck and the bristles 146 are spread, a path c–d where the ends of the bristles 146 brush a tooth side upwardly in a scraping manner and move upwardly while being spread, and a path d–a where the ends of the bristles 146 are closed).

Since the bristles 146 are closed as they are lowered, they do not peel off the end of the gum. When the bristles 146 are elevated, they can scrape plaque deposited on the tooth neck and tooth side in the embodiment shown in FIGS. 23 and 24, the bristle bases 142 are disposed in upper, middle, and lower positions. The bristles 146 on the bristle bases 142 are longer, shorter, and medium successively from the lower position through the middle position to the upper position. With this arrangement, the bristles 146 of the bristle assembly 116 can be brought into abutment against a curved tooth surface extending from the tooth side along, the tooth neck for scraping off deposited plaque.

The bristle bases 142 may be located in upper and lower positions. In this case, the bristles 146 on the bristle base 142 in the lower position should preferably be longer than the bristles 146 on the bristle base 142 in the upper position for abutment against the curved tooth surface extending from the tooth side along the tooth neck for scraping off deposited plaque.

The bristles 146 may be planted through a coupling on the bristle bases 142 so that the bristles 146 can be replaced.

As shown in FIGS. 22 and 24, a temporary positioning member 154 for temporarily positioning the bristles 146 of the bristle assembly 116 for engagement with the tooth side and the tooth neck is mounted on the horizontal case 122 of the casing 114.

The temporary positioning member 154 has a base plate 158 fitted in a recess 122 that is defined in a lower surface of the horizontal case 122, and bristles 146 planted on a lower surface of the base plate 158. Instead of the bristles 146, a resilient member such as of sponge may be fixed in place to the base plate 158.

An adjustment screw 162 threaded through a threaded hole 160 defined in the horizontal case 122 has a lower end loosely engaging the base plate 158 that is fitted in the recess 156. When the adjustment screw 162 is turned in one direction or the other, the base plate 158 is vertically slid in the recess 156 for thereby adjusting the height of the bristles 146.

When the bristles 146 of the temporary positioning member 154 is held in abutment against the occlusal area of the crown of a tooth, the bristles 146 of the bristle assembly 116 that project from the inner side wall of the vertical case 120 are accurately brought into abutment against the tooth side and the tooth neck, allowing the bristle assembly 116 to brush the tooth upon reciprocating angular movement.

As shown in FIGS. 22 and 23, the casing 114 has joint sleeves 164 extending from upper portions of its opposite ends for detachably joining handle 112. In the joint sleeves 164, there are disposed respective gears 166 fixed to respective opposite ends of the rotatable shaft 126 of the reciprocally rocking mechanism 118 which project into the joint sleeves 164.

The handle 112 comprises a cylindrical body 170 detachably joined to one of the joint sleeves 164 and housing an actuator 168, and a grip cylinder 174 detachably joined to the cylindrical body 170 and housing a battery 172 or a booster or the like for converting AC electric energy into DC electric energy.

The actuator 168 comprises a small motor 176 having a rotatable shaft to which a gear 178 is fixed, and a gear 166 fixed to the rotatable shaft 126 in the joint sleeve 164 is held in mesh with the gear 178. When a switch 180 mounted on an upper surface of the cylindrical body 170 is turned on, the small motor 176 is energized to actuate the reciprocally rocking mechanism 118 in the casing 114. The joined ends of the joint sleeve 164 and the cylindrical body 170 should preferably be reinforced by a reinforcing band 182 mounted thereon.

Figure 29:
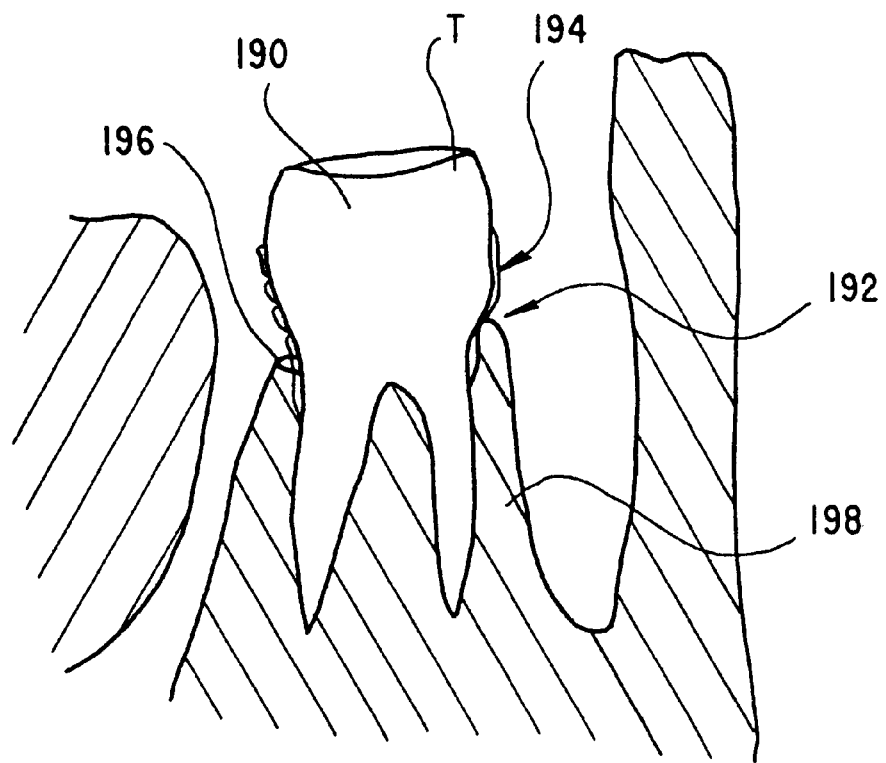
FIG. 29 is a view illustrative of the structure of a tooth.

The electric toothbrush 100 according to the present invention is used as follows. While the user is gripping the handle 112, the user holds the temporary positioning member 154 against the occlusal area of the crown 190 of a tooth T for thereby positioning the tip ends of the bristles 146 of the bristle assembly 116 in abutment against the tooth side to the tooth neck 192 of the tooth T, as shown in FIGS. 24 and 29.

Then, the user turns on the switch 180 on the handle 112 to cause the small motor 176 of the actuator 168 to rotate the rotatable shaft 126 in the casing 114. The swing shafts 128 of the reciprocally rocking mechanism 118 are moved vertically, causing the bristle bases 142 of the bristle assembly 116 coupled to the swing shafts 128 to angularly move reciprocally.

The tip ends of the bristles 146 are angularly moved reciprocally in a manner to turn upwardly to scrape off plaque 194 deposited on the tooth side and the tooth neck without pushing the plaque into a gum groove 196. The bristles 146 are also effective to massage the gum 198. The temporary positioning member 154 of the casing 114 is moved along the occlusal areas of upper and lower teeth in abutment there against for thereby removing plaque deposited on the tooth side and the tooth neck of each tooth T.

When the electric toothbrush 100 is to be used on the back of teeth T or the opposite side of the teeth, the cylindrical member 170 of the handle 112 is fitted over the joint sleeve 164 on the other end of the casing 114.

When the electric toothbrush 100 according to the present invention is used, therefore, the gum is prevented from being peeled off the tooth necks, and hence can be maintained in a healthy condition for protection against periodontites and dental caries.

Figure 28:
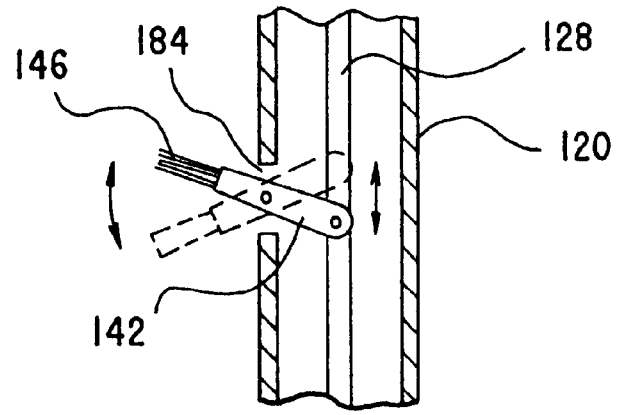
FIG. 28 is a fragmentary vertical cross-sectional view of a brush assembly according to another embodiment.

As shown in FIG. 28, the lower end of each brush base 142 may be pivotally coupled to the swing shafts 128 in the vertical case 120 and the sides of each brush base 142 may be pivotally mounted in a lateral hole 184 defined in the inner side wall of the vertical case 120. When the swing shafts 128 are moved vertically, the brush base 142 is angularly moved to cause the bristles 146 on the end of the brush base 142 to remove plaque and tartar deposited on the tooth side and the tooth neck of each tooth T.

With the electric toothbrush 100 according to the present invention, the casing 114 may not necessarily be limited to an inverted L shape, but may be of a shape spreading at an obtuse angle. Furthermore, only the vertical case 120 may serve as a casing with the bristle assembly 116 housed therein. Such an arrangement is easier to use.

The present invention with the above arrangement offers the following advantages:

(a) The bristle assemblies of a toothbrush are inclined at a certain angle with respect to the sides of teeth toward the tip ends of the teeth that are fitted between the bristle assemblies. Therefore, when the teeth are fitted in the tooth fitting portion to bring the tip ends of the bristle assemblies into abutment against the teeth surfaces, and the bristle assemblies are angularly moved reciprocally, the frictional force applied by the bristle assemblies is stronger upon angular movement toward the tip ends of the teeth, and weaker upon angular movement in the opposite direction. Therefore, plaque, tartar, and calculus deposited on the occlusal tooth areas, the tooth sides, and the tooth necks are gathered toward the center of the tooth fitting portion by the bristle assemblies, and efficiently removed.

(b) As described above, when the bristle assemblies are angularly moved reciprocally, the frictional force applied by the bristle assemblies is stronger upon angular movement toward the tip ends of the teeth, and weaker upon angular movement in the opposite direction. Therefore, even when the tooth necks are brushed, the gum is not peeled off the tooth necks, and plaque, tartar, and calculus deposited on the tooth necks are not pushed between the teeth and the gum, and do not cause periodontites.

(c) The electric toothbrush can brush teeth more efficiently than the manually operable toothbrush because the bristle assemblies can be angularly moved reciprocally at higher speeds.

(d) With the toothbrush including the adjusting means, the projection of the bristle assembly can be adjusted by the adjusting means such that the bristle assembly adjustable by the adjusting means will abut against the occlusal tooth areas of teeth and the other bristle assemblies will abut reliably against the boundaries (the tooth necks) between the tooth sides and the gum. The toothbrush can thus accommodate various lengths, which differ from individual to individual, of teeth projecting from the gum, and is capable of brushing teeth effectively in a manner to suit the user.

(e) The electric toothbrushes according to the tenth through sixteenth inventions have a bristle assembly reciprocally angularly movable to swing upwardly along teeth sides while being held against the teeth sides or neighboring regions, a reciprocally rocking mechanism for reciprocally angularly moving the bristle assembly, and an actuator coupled to the reciprocally rocking mechanism. When the bristle assembly held against the tooth sides and the tooth necks are repeatedly turned upwardly, the gum is prevented from being peeled off the tooth necks, and hence can be maintained in a healthy condition. The bristle assembly can efficiently scrape plaque off upwardly along the tooth sides and the tooth necks for protection against periodontites and dental caries.

I claim:

1. A toothbrush comprising:

an elongated handle having an axis, a central brush head formed at an end of said handle, said central brush head being disposed centrally with respect to a vertical plane extending through said axis of said handle and having a fixed orientation with respect to said vertical plane; and a lateral brush head disposed laterally with respect to said vertical plane, said lateral brush head having bristle assemblies extending substantially at right angle with respect to a bristle assembly planted surface thereof, said lateral brush head being connected to said central brush head by connecting means, said bristle assembly planted surface of said lateral brush head lying in a plane obliquely intersecting said vertical plane such that said bristle assembly planted surface of said lateral brush head has an upper level side edge located away from said vertical plane and a lower level side edge located close to said vertical plane, said connecting means having an upper end connected to said central brush head, a lower end connected to said lateral brush head and a curved portion intermediary between said upper and lower ends, said curved portion and said lower end of said connecting means having a positional relation such that said curved portion is located away from said vertical plane while said lower end is located close to said vertical plane, wherein said central brush head includes a bristle assembly supporting element having a bristle assembly planted surface which lies on a plane extending substantially perpendicularly to said vertical plane, said bristle assembly supporting element is movable with respect to said central brush head substantially along said vertical plane such that a position of said bristle assembly planted surface of said central brush head is set by vertically adjusting said position.

2. A toothbrush according to claim 1, wherein said connecting means comprises a plate connecting an outer surface of said central brush head to an outer surface of said lateral brush head.

3. A toothbrush according to claim 2, wherein said plate is removably fastened to said central and lateral brush heads by fastening means.

4. A toothbrush according to claim 2, wherein said plate covers said outer surfaces of said central brush head and said lateral brush head.

5. A toothbrush according to claim 1, further comprising a second lateral brush head disposed laterally with respect to said vertical plane, wherein said lateral brush heads are disposed on opposite sides of said central brush head.

6. A toothbrush according to claim 1, wherein an angle of said bristle assemblies of said lateral brush head with respect to said vertical plane is in the range from substantially 30° to substantially 60°.

* * * * *